(12) United States Patent
Luo et al.

(10) Patent No.: US 8,389,684 B2
(45) Date of Patent: Mar. 5, 2013

(54) TUMOR BIOMARKER

(75) Inventors: Yongzhang Luo, Beijing (CN); Xiaomin Song, Beijing (CN); Xiaofeng Wang, Beijing (CN); Wei Zhuo, Beijing (CN); Guodong Chang, Beijing (CN); Yan Fu, Beijing (CN)

(73) Assignees: Tsinghua University, Beijing (CN); Protgen Ltd., Beijing (CN)

( * ) Notice: Subject to any disclaimer, the term of this patent is extended or adjusted under 35 U.S.C. 154(b) by 232 days.

(21) Appl. No.: 12/880,265

(22) Filed: Sep. 13, 2010

(65) Prior Publication Data

US 2012/0064078 A1 Mar. 15, 2012

(51) Int. Cl.
- *C07K 1/00* (2006.01)
- *C07K 14/00* (2006.01)
- *C07K 17/00* (2006.01)
- *G01N 33/00* (2006.01)

(52) U.S. Cl. .......................................... 530/350; 436/86

(58) Field of Classification Search ........................ None
See application file for complete search history.

*Primary Examiner* — Alana Harris Dent
(74) *Attorney, Agent, or Firm* — Rothwell, Figg, Ernst & Manbeck, P.C.

(57) ABSTRACT

The present invention relates to the diagnosis and treatment of cancer, and specifically to a method of diagnosing the presence or metastasis of cancer by detecting plasma Hsp90α having the amino acid sequence of SEQ ID No. 1 as a tumor marker. In addition, the present invention also relates to a method for the treatment of cancer and metastasis.

3 Claims, 17 Drawing Sheets

A

B

SEQUENCE LISTING

<160> NUMBER OF SEQ ID NOS: 20

<210> SEQ ID NO 1
<211> LENGTH: 728
<212> TYPE: PRT
<213> ORGANISM: Homo sapiens
<220> FEATURE:
<221> NAME/KEY: Phosphorylation
<222> LOCATION: (90)..(90)
<223> OTHER INFORMATION: Optional phosphorylation at amino acid residue
      Thr 90
<220> FEATURE:
<221> NAME/KEY: Phosphorylation
<222> LOCATION: (231)..(231)
<223> OTHER INFORMATION: Optional phosphorylation at amino acid residue
      Ser 231
<220> FEATURE:
<221> NAME/KEY: Phosphorylation
<222> LOCATION: (263)..(263)
<223> OTHER INFORMATION: Optional phosphorylation at amino acid residue
      Ser 263
<220> FEATURE:
<221> NAME/KEY: Phosphorylation
<222> LOCATION: (309)..(309)
<223> OTHER INFORMATION: Optional phosphorylation at amino acid residue
      Tyr 309

<400> SEQUENCE: 1

Met Pro Glu Glu Thr Gln Thr Gln Asp Gln Pro Met Glu Glu Glu
1               5                   10                  15

Val Glu Thr Phe Ala Phe Gln Ala Glu Ile Ala Gln Leu Met Ser Leu
                20                  25                  30

Ile Ile Asn Thr Phe Tyr Ser Asn Lys Glu Ile Phe Leu Arg Glu Leu
            35                  40                  45

Ile Ser Asn Ser Ser Asp Ala Leu Asp Lys Ile Arg Tyr Glu Thr Leu
        50                  55                  60

Thr Asp Pro Ser Lys Leu Asp Ser Gly Lys Glu Leu His Ile Asn Leu
65                  70                  75                  80

Ile Pro Asn Lys Gln Asp Arg Thr Leu Thr Ile Val Asp Thr Gly Ile
                85                  90                  95

Gly Met Thr Lys Ala Asp Leu Ile Asn Asn Leu Gly Thr Ile Ala Lys
            100                 105                 110

Ser Gly Thr Lys Ala Phe Met Glu Ala Leu Gln Ala Gly Ala Asp Ile
        115                 120                 125

Ser Met Ile Gly Gln Phe Gly Val Gly Phe Tyr Ser Ala Tyr Leu Val
    130                 135                 140

Ala Glu Lys Val Thr Val Ile Thr Lys His Asn Asp Asp Glu Gln Tyr
145                 150                 155                 160

Ala Trp Glu Ser Ser Ala Gly Gly Ser Phe Thr Val Arg Thr Asp Thr
                165                 170                 175

Gly Glu Pro Met Gly Arg Gly Thr Lys Val Ile Leu His Leu Lys Glu
            180                 185                 190

Asp Gln Thr Glu Tyr Leu Glu Glu Arg Arg Ile Lys Glu Ile Val Lys
        195                 200                 205

Lys His Ser Gln Phe Ile Gly Tyr Pro Ile Thr Leu Phe Val Glu Lys
    210                 215                 220

Glu Arg Asp Lys Glu Val Ser Asp Asp Glu Ala Glu Lys Glu Glu Asp
225                 230                 235                 240

Lys Glu Glu Glu Lys Lys Glu Glu Lys Glu Ser Glu Asp Lys Pro
                245                 250                 255

-continued

```
Glu Ile Glu Asp Val Gly Ser Asp Glu Glu Lys Lys Asp Gly
            260                 265                 270
Asp Lys Lys Lys Lys Lys Ile Lys Lys Tyr Ile Asp Gln Glu
        275                 280                 285
Glu Leu Asn Lys Thr Lys Pro Ile Trp Thr Arg Asn Pro Asp Ile
    290                 295                 300
Thr Asn Glu Glu Tyr Gly Glu Phe Tyr Lys Ser Leu Thr Asn Asp Trp
305                 310                 315                 320
Glu Asp His Leu Ala Val Lys His Phe Ser Val Gly Gln Leu Glu
                325                 330                 335
Phe Arg Ala Leu Leu Phe Val Pro Arg Arg Ala Pro Phe Asp Leu Phe
            340                 345                 350
Glu Asn Arg Lys Lys Lys Asn Asn Ile Lys Leu Tyr Val Arg Arg Val
            355                 360                 365
Phe Ile Met Asp Asn Cys Glu Glu Leu Ile Pro Glu Tyr Leu Asn Phe
            370                 375                 380
Ile Arg Gly Val Val Asp Ser Glu Asp Leu Pro Leu Asn Ile Ser Arg
385                 390                 395                 400
Glu Met Leu Gln Gln Ser Lys Ile Leu Lys Val Ile Arg Lys Asn Leu
                405                 410                 415
Val Lys Lys Cys Leu Glu Leu Phe Thr Glu Leu Ala Glu Asp Lys Glu
            420                 425                 430
Asn Tyr Lys Lys Phe Tyr Glu Gln Phe Ser Lys Asn Ile Lys Leu Gly
            435                 440                 445
Ile His Glu Asp Ser Gln Asn Arg Lys Lys Leu Ser Glu Leu Leu Arg
    450                 455                 460
Tyr Tyr Thr Ser Ala Ser Gly Asp Glu Met Val Ser Leu Lys Asp Tyr
465                 470                 475                 480
Cys Thr Arg Met Lys Glu Asn Gln Lys His Ile Tyr Tyr Ile Thr Gly
                485                 490                 495
Glu Thr Lys Asp Gln Val Ala Asn Ser Ala Phe Val Glu Arg Leu Arg
            500                 505                 510
Lys His Gly Leu Glu Val Ile Tyr Met Ile Glu Pro Ile Asp Glu Tyr
        515                 520                 525
Cys Val Gln Gln Leu Lys Glu Phe Glu Gly Lys Thr Leu Val Ser Val
    530                 535                 540
Thr Lys Glu Gly Leu Glu Leu Pro Glu Asp Glu Glu Lys Lys Lys
545                 550                 555                 560
Gln Glu Glu Lys Lys Thr Lys Phe Glu Asn Leu Cys Lys Ile Met Lys
                565                 570                 575
Asp Ile Leu Glu Lys Lys Val Glu Lys Val Val Val Ser Asn Arg Leu
            580                 585                 590
Val Thr Ser Pro Cys Cys Ile Val Thr Ser Thr Tyr Gly Trp Thr Ala
            595                 600                 605
Asn Met Glu Arg Ile Met Lys Ala Gln Ala Leu Arg Asp Asn Ser Thr
    610                 615                 620
Met Gly Tyr Met Ala Ala Lys Lys His Leu Glu Ile Asn Pro Asp His
625                 630                 635                 640
Ser Ile Ile Glu Thr Leu Arg Gln Lys Ala Glu Ala Asp Lys Asn Asp
                645                 650                 655
Lys Ser Val Lys Asp Leu Val Ile Leu Leu Tyr Glu Thr Ala Leu Leu
            660                 665                 670
Ser Ser Gly Phe Ser Leu Glu Asp Pro Gln Thr His Ala Asn Arg Ile
            675                 680                 685
```

Tyr Arg Met Ile Lys Leu Gly Leu Gly Ile Asp Glu Asp Pro Thr
    690              695                 700

Ala Asp Asp Thr Ser Ala Ala Val Thr Glu Glu Met Pro Pro Leu Glu
705                 710                 715                 720

Gly Asp Asp Asp Thr Ser Arg Met
            725

<210> SEQ ID NO 2
<211> LENGTH: 2184
<212> TYPE: DNA
<213> ORGANISM: Homo sapiens

<400> SEQUENCE: 2

| | | | | | |
|---|---|---|---|---|---|
| atgcctgagg | aaacccagac | ccaagaccaa | ccgatggagg | aggaggaggt | tgagacgttc | 60 |
| gcctttcagg | cagaaattgc | ccagttgatg | tcattgatca | tcaatacttt | ctactcgaac | 120 |
| aaagagatct | ttctgagaga | gctcatttca | aattcatcag | atgcattgga | caaaatccgg | 180 |
| tatgaaactt | tgacagatcc | cagtaaatta | gactctggga | agagctgca | tattaacctt | 240 |
| ataccgaaca | aacaagatcg | aactctcact | attgtggata | ctggaattgg | aatgaccaag | 300 |
| gctgacttga | tcaataacct | tggtactatc | gccaagtctg | gaccaaagc | gttcatggaa | 360 |
| gctttgcagg | ctggtgcaga | tatctctatg | attggccagt | tcgtgttgg | ttttattct | 420 |
| gcttatttgg | ttgctgagaa | agtaactgtg | atcaccaaac | ataacgatga | tgagcagtac | 480 |
| gcttgggagt | cctcagcagg | gggatcattc | acagtgagga | cagacacagg | tgaacctatg | 540 |
| ggtcgtggaa | caaaagttat | cctacacctg | aaagaagacc | aaactgagta | cttggaggaa | 600 |
| cgaagaataa | aggagattgt | gaagaaacat | tctcagttta | ttggatatcc | cattactctt | 660 |
| tttgtggaga | aggaacgtga | taagaagta | agcgatgatg | aggctgaaga | aaaggaagac | 720 |
| aaagaagaag | aaaaagaaaa | agaagagaaa | gagtcggaag | acaaacctga | aattgaagat | 780 |
| gttggttctg | atgaggaaga | agaaaagaag | gatggtgaca | gaagaagaa | gaagaagatt | 840 |
| aaggaaaagt | acatcgatca | agaagagctc | aacaaaacaa | agcccatctg | gaccagaaat | 900 |
| cccgacgata | ttactaatga | ggagtacgga | gaattctata | agagcttgac | caatgactgg | 960 |
| gaagatcact | tggcagtgaa | gcattttttca | gttgaaggac | agttggaatt | cagagccctt | 1020 |
| ctatttgtcc | cacgacgtgc | tccttttgat | ctgtttgaaa | acagaaagaa | aaagaacaat | 1080 |
| atcaaattgt | atgtacgcag | agttttcatc | atggataact | gtgaggagct | aatccctgaa | 1140 |
| tatctgaact | tcattagagg | ggtggtagac | tcggaggatc | tccctctaaa | catatcccgt | 1200 |
| gagatgttgc | aacaaagcaa | aattttgaaa | gttatcagga | agaaatttggt | caaaaaatgc | 1260 |
| ttagaactct | ttactgaact | ggcggaagat | aagagaact | caagaaatt | ctatgagcag | 1320 |
| ttctctaaaa | acataaagct | tggaatacac | gaagactctc | aaaatcggaa | gaagcttttca | 1380 |
| gagctgttaa | ggtactacac | atctgcctct | ggtgatgaga | tggtttctct | caaggactac | 1440 |
| tgcaccagaa | tgaaggagaa | ccagaaacat | atctattata | tcacaggtga | gaccaaggac | 1500 |
| caggtagcta | actcagcctt | tgtggaacgt | cttcggaaac | atggcttaga | agtgatctat | 1560 |
| atgattgagc | ccattgatga | gtactgtgtc | caacagctga | aggaatttga | ggggaagact | 1620 |
| ttagtgtcag | tcaccaaaga | aggcctgaa | cttccagagg | atgaagaaga | gaaaagaag | 1680 |
| caggaagaga | aaaaaacaaa | gtttgagaac | ctctgcaaaa | tcatgaaaga | catattggag | 1740 |
| aaaaaagttg | aaaaggtggt | tgtgtcaaac | cgattggtga | catctccatg | ctgtattgtc | 1800 |
| acaagcacat | atggctggac | agcaaacatg | gagagaatca | tgaaagctca | agcccctaaga | 1860 |

-continued

```
gacaactcaa caatgggtta catggcagca agaaacacc tggagataaa ccctgaccat    1920
tccattattg agaccttaag gcaaaaggca gaggctgata agaacgacaa gtctgtgaag    1980
gatctggtca tcttgcttta tgaaactgcg ctcctgtctt ctggcttcag tctggaagat    2040
ccccagacac atgctaacag gatctacagg atgatcaaac ttggtctggg tattgatgaa    2100 gatgaccta ctgctgatga taccagtgct gctgtaactg aagaaatgcc accccttgaa    2160
ggagatgacg acacatcacg catg                                          2184

<210> SEQ ID NO 3
<211> LENGTH: 732
<212> TYPE: PRT
<213> ORGANISM: Homo sapiens

<400> SEQUENCE: 3

Met Pro Glu Glu Thr Gln Thr Gln Asp Gln Pro Met Glu Glu Glu
1               5                   10                  15

Val Glu Thr Phe Ala Phe Gln Ala Glu Ile Ala Gln Leu Met Ser Leu
            20                  25                  30

Ile Ile Asn Thr Phe Tyr Ser Asn Lys Glu Ile Phe Leu Arg Glu Leu
        35                  40                  45

Ile Ser Asn Ser Ser Asp Ala Leu Asp Lys Ile Arg Tyr Glu Thr Leu
    50                  55                  60

Thr Asp Pro Ser Lys Leu Asp Ser Gly Lys Glu Leu His Ile Asn Leu
65                  70                  75                  80

Ile Pro Asn Lys Gln Asp Arg Thr Leu Thr Ile Val Asp Thr Gly Ile
                85                  90                  95

Gly Met Thr Lys Ala Asp Leu Ile Asn Asn Leu Gly Thr Ile Ala Lys
            100                 105                 110

Ser Gly Thr Lys Ala Phe Met Glu Ala Leu Gln Ala Gly Ala Asp Ile
        115                 120                 125

Ser Met Ile Gly Gln Phe Gly Val Gly Phe Tyr Ser Ala Tyr Leu Val
    130                 135                 140

Ala Glu Lys Val Thr Val Ile Thr Lys His Asn Asp Asp Glu Gln Tyr
145                 150                 155                 160

Ala Trp Glu Ser Ser Ala Gly Gly Ser Phe Thr Val Arg Thr Asp Thr
                165                 170                 175

Gly Glu Pro Met Gly Arg Gly Thr Lys Val Ile Leu His Leu Lys Glu
            180                 185                 190

Asp Gln Thr Glu Tyr Leu Glu Glu Arg Arg Ile Lys Glu Ile Val Lys
        195                 200                 205

Lys His Ser Gln Phe Ile Gly Tyr Pro Ile Thr Leu Phe Val Glu Lys
    210                 215                 220

Glu Arg Asp Lys Glu Val Ser Asp Asp Glu Ala Glu Glu Lys Glu Asp
225                 230                 235                 240

Lys Glu Glu Glu Lys Glu Lys Glu Glu Lys Glu Ser Glu Asp Lys Pro
                245                 250                 255

Glu Ile Glu Asp Val Gly Ser Asp Glu Glu Glu Glu Lys Lys Asp Gly
            260                 265                 270

Asp Lys Lys Lys Lys Lys Lys Ile Lys Glu Lys Tyr Ile Asp Gln Glu
        275                 280                 285

Glu Leu Asn Lys Thr Lys Pro Ile Trp Thr Arg Asn Pro Asp Asp Ile
    290                 295                 300

Thr Asn Glu Glu Tyr Gly Glu Phe Tyr Lys Ser Leu Thr Asn Asp Trp
305                 310                 315                 320
```

```
Glu Asp His Leu Ala Val Lys His Phe Ser Val Gly Gln Leu Glu
                325                 330                 335

Phe Arg Ala Leu Leu Phe Val Pro Arg Ala Pro Phe Asp Leu Phe
                340                 345                 350

Glu Asn Arg Lys Lys Asn Asn Ile Lys Leu Tyr Val Arg Arg Val
                355                 360                 365

Phe Ile Met Asp Asn Cys Glu Glu Leu Ile Pro Glu Tyr Leu Asn Phe
370                 375                 380

Ile Arg Gly Val Val Asp Ser Glu Asp Leu Pro Leu Asn Ile Ser Arg
385                 390                 395                 400

Glu Met Leu Gln Gln Ser Lys Ile Leu Lys Val Ile Arg Lys Asn Leu
                405                 410                 415

Val Lys Lys Cys Leu Glu Leu Phe Thr Glu Leu Ala Glu Asp Lys Glu
                420                 425                 430

Asn Tyr Lys Lys Phe Tyr Glu Gln Phe Ser Lys Asn Ile Lys Leu Gly
                435                 440                 445

Ile His Glu Asp Ser Gln Asn Arg Lys Lys Leu Ser Glu Leu Leu Arg
    450                 455                 460

Tyr Tyr Thr Ser Ala Ser Gly Asp Glu Met Val Ser Leu Lys Asp Tyr
465                 470                 475                 480

Cys Thr Arg Met Lys Glu Asn Gln Lys His Ile Tyr Tyr Ile Thr Gly
                485                 490                 495

Glu Thr Lys Asp Gln Val Ala Asn Ser Ala Phe Val Glu Arg Leu Arg
                500                 505                 510

Lys His Gly Leu Glu Val Ile Tyr Met Ile Glu Pro Ile Asp Glu Tyr
                515                 520                 525

Cys Val Gln Gln Leu Lys Glu Phe Glu Gly Lys Thr Leu Val Ser Val
                530                 535                 540

Thr Lys Glu Gly Leu Glu Leu Pro Glu Asp Glu Glu Lys Lys Lys
545                 550                 555                 560

Gln Glu Glu Lys Lys Thr Lys Phe Glu Asn Leu Cys Lys Ile Met Lys
                565                 570                 575

Asp Ile Leu Glu Lys Lys Val Glu Lys Val Val Ser Asn Arg Leu
                580                 585                 590

Val Thr Ser Pro Cys Cys Ile Val Thr Ser Thr Tyr Gly Trp Thr Ala
                595                 600                 605

Asn Met Glu Arg Ile Met Lys Ala Gln Ala Leu Arg Asp Asn Ser Thr
            610                 615                 620

Met Gly Tyr Met Ala Ala Lys Lys His Leu Glu Ile Asn Pro Asp His
625                 630                 635                 640

Ser Ile Ile Glu Thr Leu Arg Gln Lys Ala Glu Ala Asp Lys Asn Asp
                645                 650                 655

Lys Ser Val Lys Asp Leu Val Ile Leu Leu Tyr Glu Thr Ala Leu Leu
                660                 665                 670

Ser Ser Gly Phe Ser Leu Glu Asp Pro Gln Thr His Ala Asn Arg Ile
                675                 680                 685

Tyr Arg Met Ile Lys Leu Gly Leu Gly Ile Asp Glu Asp Pro Thr
                690                 695                 700

Ala Asp Asp Thr Ser Ala Ala Val Thr Glu Glu Met Pro Pro Leu Glu
705                 710                 715                 720

Gly Asp Asp Asp Thr Ser Arg Met Glu Glu Val Asp
                725                 730
```

<210> SEQ ID NO 4

<211> LENGTH: 2199
<212> TYPE: DNA
<213> ORGANISM: Homo sapiens

<400> SEQUENCE: 4

| | | | | | |
|---|---|---|---|---|---|
| atgcctgagg | aaacccagac | ccaagaccaa | ccgatggagg | aggaggaggt | tgagacgttc | 60 |
| gcctttcagg | cagaaattgc | ccagttgatg | tcattgatca | tcaatacttt | ctactcgaac | 120 |
| aaagagatct | ttctgagaga | gctcatttca | aattcatcag | atgcattgga | caaaatccgg | 180 |
| tatgaaactt | tgacagatcc | cagtaaatta | gactctggga | agagctgca | tattaacctt | 240 |
| ataccgaaca | aacaagatcg | aactctcact | attgtggata | ctggaattgg | aatgaccaag | 300 |
| gctgacttga | tcaataacct | tggtactatc | gccaagtctg | gaccaaaagc | gttcatggaa | 360 |
| gctttgcagc | tggtgcaga | tatctctatg | attggccagt | tcggtgttgg | tttttattct | 420 |
| gcttatttgg | ttgctgagaa | agtaactgtg | atcaccaaac | ataacgatga | tgagcagtac | 480 |
| gcttgggagt | cctcagcagg | gggatcattc | acagtgagga | cagacacagg | tgaacctatg | 540 |
| ggtcgtggaa | caaaagttat | cctacacctg | aaagaagacc | aaactgagta | cttggaggaa | 600 |
| cgaagaataa | aggagattgt | gaagaaacat | tctcagttta | ttggatatcc | cattactctt | 660 |
| tttgtggaga | aggaacgtga | taagaagta | agcgatgatg | aggctgaaga | aaggaagac | 720 |
| aaagaagaag | aaaaagaaaa | agaagagaaa | gagtcggaag | acaaacctga | aattgaagat | 780 |
| gttggttctg | atgaggaaga | agaaaagaag | gatggtgaca | gaagaagaa | gaagaagatt | 840 |
| aaggaaaagt | acatcgatca | agaagagctc | aacaaaacaa | agcccatctg | gaccagaaat | 900 |
| cccgacgata | ttactaatga | ggagtacgga | gaattctata | agagcttgac | caatgactgg | 960 |
| gaagatcact | tggcagtgaa | gcattttca | gttgaaggac | agttggaatt | cagagccctt | 1020 |
| ctatttgtcc | cacgacgtgc | tccttttgat | ctgtttgaaa | acagaagaa | aaagaacaat | 1080 |
| atcaaattgt | atgtacgcag | agttttcatc | atggataact | gtgaggagct | aatccctgaa | 1140 |
| tatctgaact | tcattagagg | ggtggtagac | tcggaggatc | tccctctaaa | catatcccgt | 1200 |
| gagatgttgc | aacaaagcaa | aattttgaaa | gttatcagga | agaatttggt | caaaaaatgc | 1260 |
| ttagaactct | ttactgaact | ggcggaagat | aaagagaact | acaagaaatt | ctatgagcag | 1320 |
| ttctctaaaa | acataaagct | tggaatacac | gaagactctc | aaaatcggaa | gaagctttca | 1380 |
| gagctgttaa | ggtactacac | atctgcctct | ggtgatgaga | tggtttctct | caaggactac | 1440 |
| tgcaccagaa | tgaaggagaa | ccagaaacat | atctattata | tcacaggtga | gaccaaggac | 1500 |
| caggtagcta | actcagcctt | tgtggaacgt | cttcggaaac | atggcttaga | agtgatctat | 1560 |
| atgattgagc | ccattgatga | gtactgtgtc | caacagctga | aggaatttga | ggggaagact | 1620 |
| ttagtgtcag | tcaccaaaga | aggcctggaa | cttccagagg | atgaagaaga | gaaaagaag | 1680 |
| caggaagaga | aaaaaacaaa | gtttgagaac | ctctgcaaaa | tcatgaaaga | catattggag | 1740 |
| aaaaaagttg | aaaaggtggt | tgtgtcaaac | cgattggtga | catctccatg | ctgtattgtc | 1800 |
| acaagcacat | atggctggac | agcaaacatg | gagagaatca | tgaaagctca | gcccctaaga | 1860 |
| gacaactcaa | caatgggtta | catggcagca | aagaaacacc | tggagataaa | ccctgaccat | 1920 |
| tccattattg | agaccttaag | gcaaaaggca | gaggctgata | agaacgacaa | gtctgtgaag | 1980 |
| gatctggtca | tcttgcttta | tgaaactgcg | ctcctgtctt | ctggcttcag | tctggaagat | 2040 |
| ccccagacac | atgctaacag | gatctacagg | atgatcaaac | ttggtctggg | tattgatgaa | 2100 |
| gatgacccta | ctgctgatga | taccagtgct | gctgtaactg | aagaaatgcc | acccttgaa | 2160 |
| ggagatgacg | acacatcacg | catggaagaa | gtagactaa | | | 2199 |

-continued

```
<210> SEQ ID NO 5
<211> LENGTH: 499
<212> TYPE: PRT
<213> ORGANISM: Homo sapiens

<400> SEQUENCE: 5

Met Ala Met Ala Glu Gly Glu Arg Thr Glu Cys Ala Glu Pro Pro Arg
1               5                   10                  15

Asp Glu Pro Pro Ala Asp Gly Ala Leu Lys Arg Ala Glu Glu Leu Lys
            20                  25                  30

Thr Gln Ala Asn Asp Tyr Phe Lys Ala Lys Asp Tyr Glu Asn Ala Ile
        35                  40                  45

Lys Phe Tyr Ser Gln Ala Ile Glu Leu Asn Pro Ser Asn Ala Ile Tyr
    50                  55                  60

Tyr Gly Asn Arg Ser Leu Ala Tyr Leu Arg Thr Glu Cys Tyr Gly Tyr
65                  70                  75                  80

Ala Leu Gly Asp Ala Thr Arg Ala Ile Glu Leu Asp Lys Lys Tyr Ile
                85                  90                  95

Lys Gly Tyr Tyr Arg Arg Ala Ala Ser Asn Met Ala Leu Gly Lys Phe
            100                 105                 110

Arg Ala Ala Leu Arg Asp Tyr Glu Thr Val Val Lys Val Lys Pro His
        115                 120                 125

Asp Lys Asp Ala Lys Met Lys Tyr Gln Glu Cys Asn Lys Ile Val Lys
    130                 135                 140

Gln Lys Ala Phe Glu Arg Ala Ile Ala Gly Asp Glu His Lys Arg Ser
145                 150                 155                 160

Val Val Asp Ser Leu Asp Ile Glu Ser Met Thr Ile Glu Asp Glu Tyr
                165                 170                 175

Ser Gly Pro Lys Leu Glu Asp Gly Lys Val Thr Ile Ser Phe Met Lys
            180                 185                 190

Glu Leu Met Gln Trp Tyr Lys Asp Gln Lys Lys Leu His Arg Lys Cys
        195                 200                 205

Ala Tyr Gln Ile Leu Val Gln Val Lys Glu Val Leu Ser Lys Leu Ser
    210                 215                 220

Thr Leu Val Glu Thr Thr Leu Lys Glu Thr Glu Lys Ile Thr Val Cys
225                 230                 235                 240

Gly Asp Thr His Gly Gln Phe Tyr Asp Leu Leu Asn Ile Phe Glu Leu
                245                 250                 255

Asn Gly Leu Pro Ser Glu Thr Asn Pro Tyr Ile Phe Asn Gly Asp Phe
            260                 265                 270

Val Asp Arg Gly Ser Phe Ser Val Glu Val Ile Leu Thr Leu Phe Gly
        275                 280                 285

Phe Lys Leu Leu Tyr Pro Asp His Phe His Leu Leu Arg Gly Asn His
    290                 295                 300

Glu Thr Asp Asn Met Asn Gln Ile Tyr Gly Phe Glu Gly Glu Val Lys
305                 310                 315                 320

Ala Lys Tyr Thr Ala Gln Met Tyr Glu Leu Phe Ser Glu Val Phe Glu
                325                 330                 335

Trp Leu Pro Leu Ala Gln Cys Ile Asn Gly Lys Val Leu Ile Met His
            340                 345                 350

Gly Gly Leu Phe Ser Glu Asp Gly Val Thr Leu Asp Asp Ile Arg Lys
        355                 360                 365

Ile Glu Arg Asn Arg Gln Pro Pro Asp Ser Gly Pro Met Cys Asp Leu
    370                 375                 380
```

| | | | | | | | | | | | | | | |
|---|---|---|---|---|---|---|---|---|---|---|---|---|---|---|
|Leu|Trp|Ser|Asp|Pro|Gln|Pro|Gln|Asn|Gly|Arg|Ser|Ile|Ser|Lys|Arg|
|385| | | | |390| | | | |395| | | | |400|

| | | | | | | | | | | | | |
|---|---|---|---|---|---|---|---|---|---|---|---|---|
|Gly|Val|Ser|Cys|Gln|Phe|Gly|Pro|Asp|Val|Thr|Lys|Ala|Phe|Leu|Glu|
| | | | |405| | | | |410| | | | |415|

Glu Asn Asn Leu Asp Tyr Ile Ile Arg Ser His Glu Val Lys Ala Glu
              420                 425                 430

Gly Tyr Glu Val Ala His Gly Gly Arg Cys Val Thr Val Phe Ser Ala
              435                 440                 445

Pro Asn Tyr Cys Asp Gln Met Gly Asn Lys Ala Ser Tyr Ile His Leu
              450                 455                 460

Gln Gly Ser Asp Leu Arg Pro Gln Phe His Gln Phe Thr Ala Val Pro
465                 470                 475                 480

His Pro Asn Val Lys Pro Met Ala Tyr Ala Asn Thr Leu Leu Gln Leu
              485                 490                 495

Gly Met Met

<210> SEQ ID NO 6
<211> LENGTH: 1500
<212> TYPE: DNA
<213> ORGANISM: Homo sapiens

<400> SEQUENCE: 6

```
atggcgatgg cggagggcga gaggactgag tgtgctgagc cccccgggga cgaaccccg        60
gctgatggag ctctgaagcg ggcagaggag ctcaagactc aggccaatga ctacttcaaa      120
gccaaggact acgagaacgc catcaagttc tacagccagg ccatcgagct gaaccccagc      180
aatgccatct actatggcaa ccgcagcctg gcctacctgc gcactgagtg ctatggctac      240
gcgctgggag acgccacgcg ggccattgag ctggacaaga agtacatcaa gggttattac      300
cgccgggctg ccagcaacat ggcactgggc aagttccggg ccgcgctgcg agactacgag      360
acggtggtca aggtgaagcc ccatgacaag gatgccaaaa tgaaatacca ggagtgcaac      420
aagatcgtga agcagaaggc cttgagcgg gccatcgcgg gcgacgagca aagcgctcc       480
gtggtggact cgctggacat cgagagcatg accattgagg atgagtacag cggacccaag      540
cttgaagacg gcaaagtgac aatcagtttc atgaaggagc tcatgcagtg gtacaaggac      600
cagaagaaac tgcaccggaa atgtgcctac cagattctgg tacaggtcaa agaggtcctc      660
tccaagctga gcacgctcgt ggaaaccaca ctcaaagaga cagagaagat tacagtatgt      720
ggggacaccc catggccagtt ctatgacctc ctcaacatat cgagctcaa cggtttaccc      780
tcggagacca ccccctatat atttaatggt gactttgtgg accgaggctc cttctctgta      840
gaagtgatcc tcacccttttt cggcttcaag ctcctgtacc cagatcactt tcacctcctt      900
cgaggcaacc acgagacaga caacatgaac cagatctacg gtttcgaggg tgaggtgaag      960
gccaagtaca cagcccagat gtacgagctc tttagcgagg tgttcgagtg gctcccgttg     1020
gcccagtgca tcaacggcaa agtgctgatc atgcacggag gcctgttcag tgaagacggt     1080
gtcaccctgg atgacatccg gaaaattgag cggaatcgac accccccaga ttcagggccc     1140
atgtgtgacc tgctctggtc agatccacag ccacagaacg ggcgctcgat cagcaagcgg     1200
ggcgtgagct gtcagtttgg gcctgacgtc accaaggcct tcttggaaga gaacaacctg     1260
gactatatca tccgcagcca cgaagtcaag gccgagggct acgaggtggc tcacggaggc     1320
cgctgtgtca ccgtcttctc tgcccccaac tactgcgacc agatggggaa caaagcctcc     1380
tacatccacc tccagggctc tgacctacgg cctcagttcc accagttcac agcagtgcct     1440
catcccaacg tcaagcccat ggcctatgcc aacacgctgc tgcagctagg aatgatgtga     1500
```

<210> SEQ ID NO 7
<211> LENGTH: 25
<212> TYPE: DNA
<213> ORGANISM: Artificial Sequence
<220> FEATURE:
<223> OTHER INFORMATION: Target sequence of Protien Posphatase 5 siRNA

<400> SEQUENCE: 7
actcgaacac ctcgctaaag agctc                                        25

<210> SEQ ID NO 8
<211> LENGTH: 30
<212> TYPE: DNA
<213> ORGANISM: Artificial Sequence
<220> FEATURE:
<223> OTHER INFORMATION: Heat Shock Protein 90 alpha Sal1 Re

<400> SEQUENCE: 8
acgcgtcgac ttagtctact tcttccatgc                                   30

<210> SEQ ID NO 9
<211> LENGTH: 31
<212> TYPE: DNA
<213> ORGANISM: Artificial Sequence
<220> FEATURE:
<223> OTHER INFORMATION: Heat Shock Protein 90 alpha Sph1 For

<400> SEQUENCE: 9
acatgcatgc atgcctgagg aaacccagac c                                 31

<210> SEQ ID NO 10
<211> LENGTH: 73
<212> TYPE: DNA
<213> ORGANISM: Artificial Sequence
<220> FEATURE:
<223> OTHER INFORMATION: Heat Shock Protein 90 alpha pc3.1 Nhe1 For Myc

<400> SEQUENCE: 10
gctagctagc gccaccatgg aacaaaaact catctcagaa gaggatctgc ctgaggaaac   60
ccagacccaa gac                                                     73

<210> SEQ ID NO 11
<211> LENGTH: 91
<212> TYPE: DNA
<213> ORGANISM: Artificial Sequence
<220> FEATURE:
<223> OTHER INFORMATION: Heat Shock Protein 90 alpha pc3.1 Nhe1 For His
    Myc

<400> SEQUENCE: 11
gctagctagc gccaccatgc atcatcatca tcatcatgaa caaaaactca tctcagaaga   60
ggatctgcct gaggaaaccc agacccaaga c                                 91

<210> SEQ ID NO 12
<211> LENGTH: 34
<212> TYPE: DNA
<213> ORGANISM: Artificial Sequence
<220> FEATURE:
<223> OTHER INFORMATION: Heat Shock Protein 90 alpha pc3.1 Xho1 Re
    nostop

<400> SEQUENCE: 12
cccgctcgag tgtctacttc ttccatgcgt gatg                              34

-continued

```
<210> SEQ ID NO 13
<211> LENGTH: 37
<212> TYPE: DNA
<213> ORGANISM: Artificial Sequence
<220> FEATURE:
<223> OTHER INFORMATION: Heat Shock Protein 90 alpha EE AA

<400> SEQUENCE: 13
ggccgctcga gtgtctactg ctgccatgcg tgatgtg                              37

<210> SEQ ID NO 14
<211> LENGTH: 37
<212> TYPE: DNA
<213> ORGANISM: Artificial Sequence
<220> FEATURE:
<223> OTHER INFORMATION: Heat Shock Protein 90 alpha VD AA

<400> SEQUENCE: 14
ggccgctcga gttgctgctt cttccatgcg tgatgtg                              37

<210> SEQ ID NO 15
<211> LENGTH: 37
<212> TYPE: DNA
<213> ORGANISM: Artificial Sequence
<220> FEATURE:
<223> OTHER INFORMATION: Heat Shock Protein 90 alpha EEVD AAAA

<400> SEQUENCE: 15
ggccgctcga gttgctgctg ctgccatgcg tgatgtg                              37

<210> SEQ ID NO 16
<211> LENGTH: 33
<212> TYPE: DNA
<213> ORGANISM: Artificial Sequence
<220> FEATURE:
<223> OTHER INFORMATION: Heat Shock Protein 90 alpha Cdelta4 Xho

<400> SEQUENCE: 16
ccgctcgagt catgcgtgat gtgtcgtcat ctc                                  33

<210> SEQ ID NO 17
<211> LENGTH: 39
<212> TYPE: DNA
<213> ORGANISM: Artificial Sequence
<220> FEATURE:
<223> OTHER INFORMATION: Heat Shock Protein 90 alpha T89A Sense

<400> SEQUENCE: 17
gatcgaactc ttgcaattgt ggatactgga attggaatg                            39

<210> SEQ ID NO 18
<211> LENGTH: 39
<212> TYPE: DNA
<213> ORGANISM: Artificial Sequence
<220> FEATURE:
<223> OTHER INFORMATION: Heat Shock Protein 90 alpha T89A Antisense

<400> SEQUENCE: 18
cattccaatt ccagtatcca caattgcaag agttcgatc                            39

<210> SEQ ID NO 19
<211> LENGTH: 39
<212> TYPE: DNA
<213> ORGANISM: Artificial Sequence
<220> FEATURE:
<223> OTHER INFORMATION: Protein Phosphatase 5 NheI For

<400> SEQUENCE: 19
```

```
ctagctagca tgtacccata cgacgtccca gactacgct                      39

<210> SEQ ID NO 20
<211> LENGTH: 40
<212> TYPE: DNA
<213> ORGANISM: Artificial Sequence
<220> FEATURE:
<223> OTHER INFORMATION: Protein Phosphatase 5 XhoI Re

<400> SEQUENCE: 20
ccgctcgagt taatgatgat gatgatgatg cacgtgtacc                     40
```

TUMOR BIOMARKER

FIELD OF INVENTION

This invention relates to the diagnosis and therapy of tumor, and specifically to a novel tumor biomarker and methods and kits for the detection of cancer occurrence and metastasis. The invention also relates to methods and medicaments for the treatment of cancer and/or its metastasis.

BACKGROUND OF INVENTION

Currently, around 11 million people are diagnosed as tumor patients every year worldwide, and it is speculated that this number will increase to more than 16 million by the year of 2020. In 2005, among the 58 million deaths, 7.6 million are caused by cancer (accounting for about 13%). This number is increasing, and it is expected that 9 and 11.4 million people will die of cancer by the year of 2015 and 2030 respectively. (World Health Organization, 2006)

Tumor markers are the substances produced by tumor cells during the progression caused by gene mutation, including antigens and other bio-active substances, which can be used for the early detection of cancers as well as the monitoring of disease progression and response to a treatment (ASCO, 1996). It brings huge benefit for the clinical treatment of cancers, especially when it can be detected before any obvious clinical phenomenon or when it can be used to monitor the patients' response to certain treatment. At present, in order to better meet the clinical need, greater efforts on the research and development of tumor biomarkers are required.

The applications of most tumor biomarkers currently used in clinic are more or less restricted due to the not-so-good sensitivity and specificity. For example, the AFP level and ultra-sonic examinations are largely used for liver cancer detection. Although their sensitivities are not very high, they indeed prolong the survival rate of the patients by diagnosis of the high-risk people. The tumor antigen CA-125 has a higher sensitivity but lacks specificity. Similarly, the blood tumor biomarker CA15-3 which is used for the detection of breast cancer could hardly be used for early detection due to low sensitivity. Therefore, methods for the early detection of cancer as well as to distinguish benign and malignant tumors are currently not available in clinic. New technologies as well as new methods are required to be developed to resolve these problems.

The development of tumor proteonomics brings hope for the identification of novel tumor biomarkers. The malignant transformation of tumors always results in the change of protein expressions, which could be quantified at the protein level. Thus, a lot of information and data could be derived, by which potential biomarkers could be identified and evaluated for further development and clinical application.

Hsp90α (Heat shock protein 90α, Hsp90α) is a molecular chaperone, which functions to stabilize its client proteins in their active states. Hsp90α is one of the most abundant proteins in the eukaryotic cells accounting for about 1-2% of whole cell proteins. The intracellular Hsp90α mainly functions to stabilize its clients (i.e. estrogen receptor) and assistant their maturation (i.e. some kinases and signal proteins). However, in other physiological conditions, Hsp90α is also involved in mediating events such as the evolution of mutated proteins, rearrangement of cytoskeleton, translocation of nuclear proteins, cell proliferation and apoptosis, protein degradation, antigen processing and LPS recognition etc. Hsp90α is also related with many diseases such as cancer, autoimmune disorder and cardiovascular diseases. For example, the monoclonal antibody against the antigen of LKVIRK sequence derived from Hsp90α can be used to treat fungal-related infection, and this clinic trial is currently ongoing by the Neutec company (Trade name: Mycogrip).

It is also reported that Hsp90α could be secreted under some stimulus (Liao et al. (2000) J. Biol. Chem. 275, 189-96). As a classical intracellular protein, there is little report regarding the function of extracelluar Hsp90α. In previous reports, Hsp90α was identified to help the antigen processing in APCs and was one of the four proteins related to the lipid raft. They can interact with LPC thus trigger the intracellular response of cells. (Triantafilou et al. (2002) Trends in Immunology 23, 301-4).

Hsp90α was also found to be highly expressed in the surface of some tumor cells, including the small-cell-lung cancer cell, melanoma and liver cancer cells (Ferrarini et al. (1992) Int. J. Cancer 51, 613-19). The high expression of cell surface Hsp90α in these cells were speculated to be related with the antigen processing while direct evidence is not available.

It is also reported that Hsp90α could help the translocation of transmembrane proteins (Schlatter et al. (2002) Biochem. J. 362, 675-84), and is related with the efflux of some anti-leukemia, lung cancer, cervix cancer drugs (Rappa et al (2002) Oncol. Res. 12, 113-9 and Rappa et al (2000) Anti-cancer Drug Des 15, 127-34).

The intracellular Hsp90α is an important target for the development of anti-cancer drugs, as it is involved in the regulation of many signaling pathways which are critical for the cancer cell transformation. Inhibition of intracellular Hsp90α could result in the selective degradation of proteins related with cell proliferation, cell cycle control as well as apoptosis. Recently, some known antibiotics such as Geldanamycin, Radicicol and Coumermycin A1 are natural inhibitors of Hsp90α. A patent (WO 00/53169) describes this mechanism and proposes that preventing the interaction of chaperones with its clients could result in the inhibition of its chaperone activity. Among these antibiotics, Coumarin and its derivatives are believed to have this activity. However, these inhibitors described in patent WO 00/53169 mainly target the intracellular Hsp90α.

The analogue of Geldanamycin 17-AAG is also an inhibitor of Hsp90α and is currently under clinical trials. However, some reports show that 17-AAG could have non-specific inhibitory effects and cell toxicity by interacting with many other cellular components. In addition, due to the limited knowledge on the physiological functions of Hsp90α and its clients, direct inhibition of intracellular Hsp90α is risky.

The patent (EP1457499A1) describes the function of extracellular Hsp90α in promoting tumor cell invasion via activating the MMP-2. Based on these mechanisms, the patent proposes that inhibition of extracellular Hsp90α could prevent the tumor invasion and metastasis, and by detecting the response of tumor cells to the treatment of Hsp90α inhibitor they can deduce the invasive ability of the cells and their relationship with Hsp90α.

The inventors of patent WO/2008/070472 propose that they can monitor the anti-tumor efficacy of Hsp90α targeted therapy by detecting the plasma Hsp90α and other related factors. In this patent, they provide the relationship between the plasma Hsp90α level and the efficacy of the inhibitors including 17-AAG and 17-DMAG as well as the relationship between the level of plasma Hsp90α and tumor volume in mouse models. However, they do not provide any evidence about the exact form of plasma Hsp90α and do not demonstrate the relationship between the plasma Hsp90α level and tumor malignancy especially tumor metastasis. They do not propose the application of plasma Hsp90α as an independent tumor biomarker in tumor diagnosis and prognosis, either.

One group reported that serum Hsp90α level is related with the stages of non-small-cell lung cancer (Xu et al. (2007) J. Cancer Mol. 3, 107-112). The serum level of Hsp90α in these lung cancer patients was significantly higher than that of normal people or benign tumor patients. However, again this paper did not identify the exact form of serum Hsp90α as well as its relationship with tumor metastasis. Besides, it only investigated non-small-cell lung cancer, while the relationship between serum Hsp90α level with breast cancer, liver cancer, and pancreatic cancer is unknown. Moreover, the serum level of Hsp90α was not quantitatively measured, thus could hardly be translated to clinic development and further application.

SUMMARY OF INVENTION

This invention is based on the discovery that the plasma Hsp90α level is correlated with the development, malignancy and metastasis of many types of cancer. Accordingly, plasma Hsp90α can be used as a new tumor biomarker. The inventors found that the plasma Hsp90α is different from the intracellular Hsp90α, because the plasma Hsp90α lacks four amino acid residues at its C-terminus compared with the intracellular Hsp90α.

Therefore, in one aspect, this invention provides an isolated polypeptide comprising or consisting of the amino acid sequence of SEQ ID No. 1.

The polypeptide of this invention may be phosphorylated. In particular, in the polypeptide of this invention, one or more amino acid residues in the amino acid sequence of SEQ ID No. 1 selected from the group consisting of Thr90, Ser231, Ser263, Tyr309 and a combination thereof are phosphorylated. Preferably, the Thr90 in the polypeptide of this invention is phosphorylated.

The polypeptide of this invention may serve as a tumor biomarker. Using an agent specifically binding to the polypeptide of this invention, it is possible to detect the plasma level of this polypeptide, and thereby to determine the presence of cancers and the stage and metastasis of cancers.

Accordingly, in another aspect, this invention relates to a method of determining the presence, stage and/or metastasis of a cancer in a subject, the method comprises the step of detecting the level of a polypeptide comprising or consisting of the amino acid sequence of SEQ ID No. 1 in a plasma sample of the subject by using an agent capable of specifically binding to said polypeptide.

In yet another aspect, this invention relates to a method of screening the presence of a cancer in a high-risk population comprising the step of detecting the level of a polypeptide comprising or consisting of the amino acid sequence of SEQ ID No. 1 in a plasma sample by using an agent capable of specifically binding to said polypeptide.

In still another aspect, this invention relates to a method of determining the prognosis of a patient having a cancer comprising the step of detecting the level of a polypeptide comprising or consisting of the amino acid sequence of SEQ ID No. 1 in a plasma sample of the patient by using an agent capable of specifically binding to said polypeptide.

In a further aspect, this invention relates to method of determining the efficiency of a surgery, radiotherapy or chemotherapy treatment to a patient having a tumor comprising the step of detecting the level of a polypeptide comprising or consisting of the amino acid sequence of SEQ ID No. 1 in a plasma sample of the patient by using an agent capable of specifically binding to said polypeptide.

Preferably, the agent capable of specifically binding to the polypeptide of this invention can be a specific antibody against the polypeptide. Preferably, the antibody is a monoclonal antibody or an antigen binding fragment thereof, such as scFv, Fab, Fab' and F(ab')2. In one specific embodiment, the antibody is MAb E9 or D10 produced by the cell line deposited under CGMCC No. 2903 or 2904, respectively.

According to this invention, the antibody specifically binds to the polypeptide present in plasma. Preferably, the antibody specifically binds to a phosphorylated form of the polypeptide of the invention, said phosphorylated form of the polypeptide contains one or more phosphorylated amino acid residues in the amino acid sequence of SEQ ID No. 1 selected from the group consisting of Thr90, Ser231, Ser263, Tyr309 and a combination thereof. Preferably, the antibody specifically binds to the polypeptide which is phosphorylated at Thr90.

In another aspect, this invention relates to a method of preventing or treating cancer metastasis in a subject comprising the step of administering an inhibitor of the polypeptide of the invention to the subject. In one embodiment of this aspect, the inhibitor is a specific antibody against a polypeptide comprising or consisting of the amino acid sequence of SEQ ID No. 1. Preferably, this antibody is humanized antibody or an antigen binding fragment thereof. In one embodiment, the antibody specifically binds to a phosphorylated form of the polypeptide, said phosphorylated form of the polypeptide contains one or more phosphorylated amino acid residues in the amino acid sequence of SEQ ID No. 1 selected from the group consisting of Thr90, Ser231, Tyr309 and a combination thereof. In a preferred embodiment, the antibody specifically binds to the polypeptide which is phosphorylated at Thr90. In one specific embodiment, the antibody is MAb E9 or D10 produced by the cell line deposited under CGMCC No. 2903 or 2904, respectively.

Among the different aspects of this invention, the cancer is selected from the group consisting of lung cancer, liver cancer, gastric cancer, gastrointestinal cancer, esophagus cancer, osteosarcoma, pancreatic cancer, lymphoma, colorectal cancer, breast cancer, prostate cancer, oral cancer, nasopharyngeal cancer, cervical cancer, ovarian cancer, leukemia, malignant melanoma, sarcoma, renal cell carcinoma and cholangiocarcinoma.

This invention also involves antibodies that can specifically bind to the polypeptide of the invention which is present in plasma. In one specific embodiment, the antibody is MAb E9 or D10 produced by the cell line deposited under CGMCC No. 2903 or 2904, respectively. Preferably, the antibody of the invention is a humanized antibody or an antigen binding fragment thereof. In one embodiment, the antibody specifically binds to a phosphorylated form of the polypeptide, said phosphorylated form of the polypeptide contains one or more phosphorylated amino acid residues in the amino acid sequence of SEQ ID No. 1 selected from the group consisting of Thr90, Ser231, Ser263, Tyr309 and a combination thereof. In a preferred embodiment, the antibody specifically binds to the polypeptide which is phosphorylated at Thr90.

In another aspect, this invention relates to a method of inhibiting cancer invasiveness and metastasis, comprising the step of inhibiting the phosphorylation of intracellular Hsp90α in cancer cells. In one embodiment, this invention relates to a method of inhibiting cancer invasiveness and metastasis, comprising the step of inhibiting the phosphorylation of Hsp90α at Thr90 in cancer cells. In one specific embodiment of this aspect, the method comprises a step of overexpressing a nucleic acid molecule encoding protein phosphatase 5 in cancer cells.

A: The plasma Hsp90α level of liver cancer patients is measured by sandwich ELISA. The plasma Hsp90α level in benign tumor patients ranges from 2-10 ng/ml, mostly 2-5 ng/ml, while the plasma Hsp90α level in 69% (20/29) liver cancer patients is above 50 ng/ml, the average of which has more than 10-fold increment compared with that of benign tumor patients, which is consistent with the result of Western blotting. This indicates that the plasma Hsp90α level is positively correlated with tumor malignancy.

B: The plasma Hsp90α level of lung cancer patients is measured by sandwich ELISA. The plasma Hsp90α level in 64% (9/14) lung cancer patients is above 50 ng/ml, the average of which has more than 10-fold increment compared with that of benign tumor patients. This indicates the plasma Hsp90α level is positively correlated with tumor malignancy.

C: The plasma Hsp90α level of breast cancer patients is measured by sandwich ELISA. Compared with benign tumor patients, the highest plasma Hsp90α level is increased by more than 5-fold. Overall, the average plasma Hsp90α level in breast cancer patients shows significantly increment when compared with that in benign tumor patients.

D: The plasma Hsp90α level of pancreatic cancer patients is measured by sandwich ELISA. The plasma Hsp90α level in 100% (10/10) pancreatic cancer patients is above 50 ng/ml, the average of which has more than 10-fold increment compared with that of benign tumor patients. This indicates the plasma Hsp90α level is positively correlated with tumor malignancy.

Figure 6:
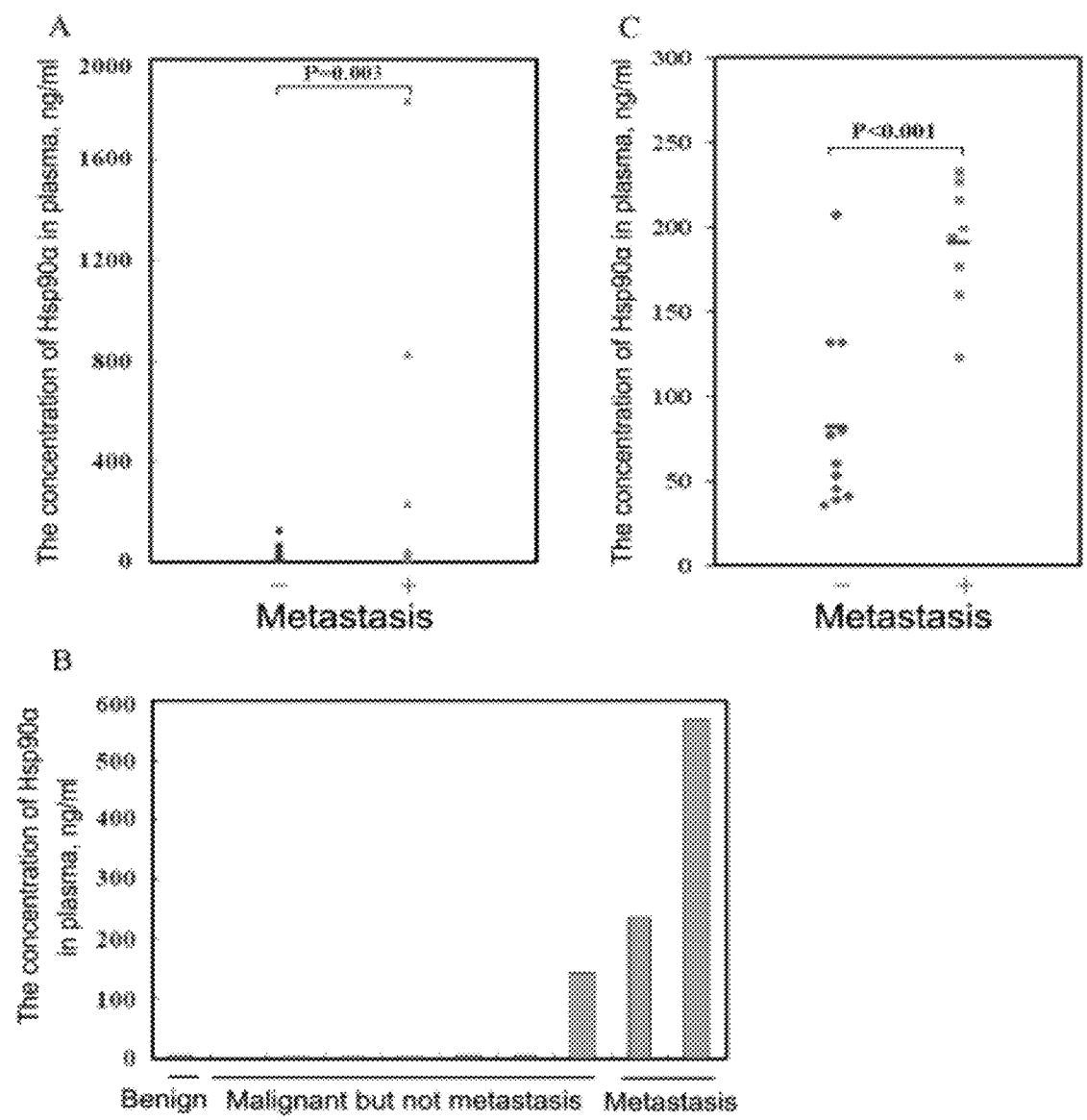

FIG. 6: Quantitative measurement of plasma Hsp90α level in the cancer patients with or without metastasis using sandwich ELISA:

A: The liver cancer patients are divided into two groups, one with metastasis and the other one without metastasis, then the plasma Hsp90α levels in these two groups are compared. The plasma Hsp90α levels in cancer patients with metastasis are all above 200 ng/ml while those in patients without metastasis range from 50-200 ng/ml.

B: The lung cancer patients are divided into two groups, one with metastasis and the other one without metastasis, then the plasma Hsp90α levels in these two groups are compared. The plasma Hsp90α levels in cancer patients with metastasis are all above 200 ng/ml while those in patients without metastasis range from 50-200 ng/ml.

C: The breast cancer patients are divided into two groups, one with metastasis and the other one without metastasis, then the plasma Hsp90α levels in these two groups are compared. The plasma Hsp90α levels in cancer patients with metastasis are significantly elevated compared with that in patients without metastasis.

Figure 7:
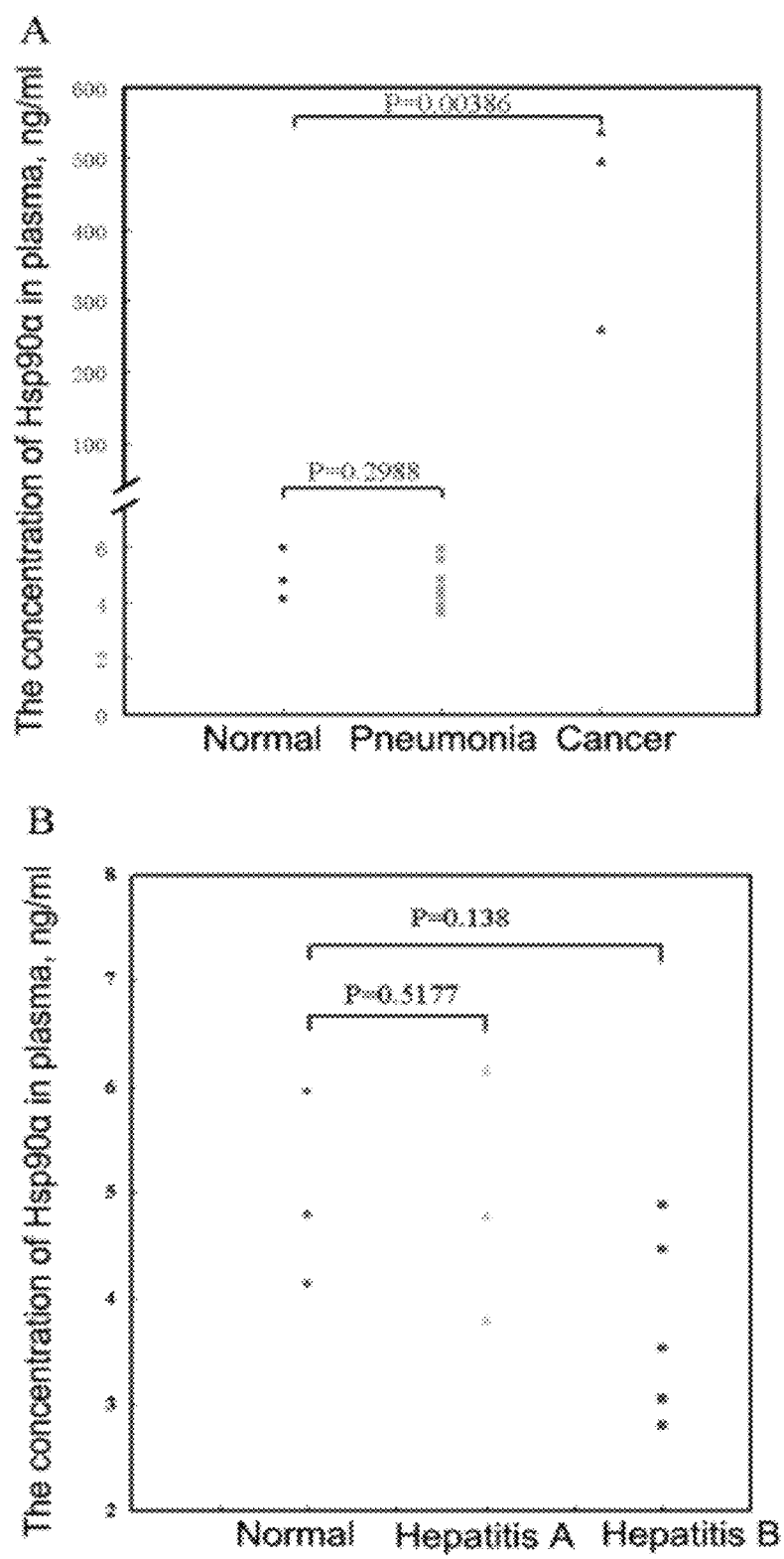

FIG. 7: Quantitative measurement of plasma Hsp90α level in the patients with inflammation (pneumonia and hepatitis), normal people and tumor patients using sandwich ELISA:

A: To ensure that the elevated plasma Hsp90α level of cancer patients is tumor specific, we compared the plasma Hsp90α level in pneumonia patients, normal people and tumor patients and found that the plasma Hsp90α level in pneumonia patients ranges from 2-10 ng/ml, indicating no significant changes compared with that in normal people.

B: The plasma Hsp90α level in hepatitis patients (Hepatitis A and B) ranges from 2-10 ng/ml, indicating no significant changes compared with that in normal people.

Figure 8:
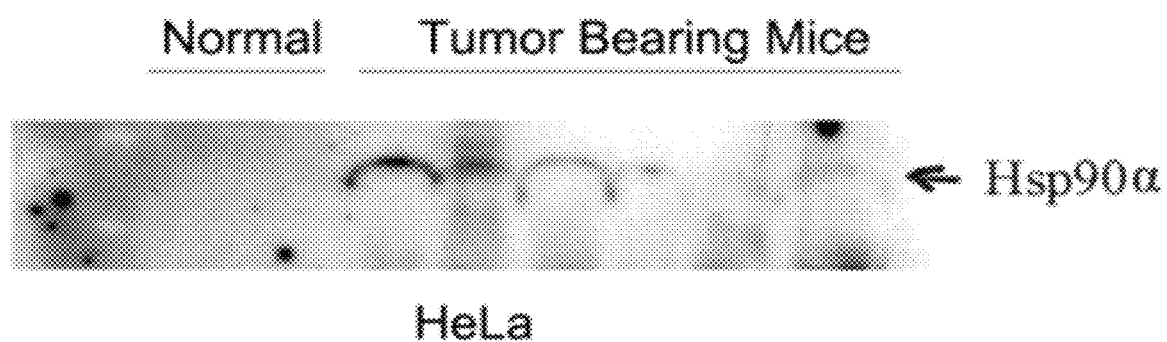

FIG. 8: The plasma Hsp90α is secreted by tumor cells.

Figure 9:
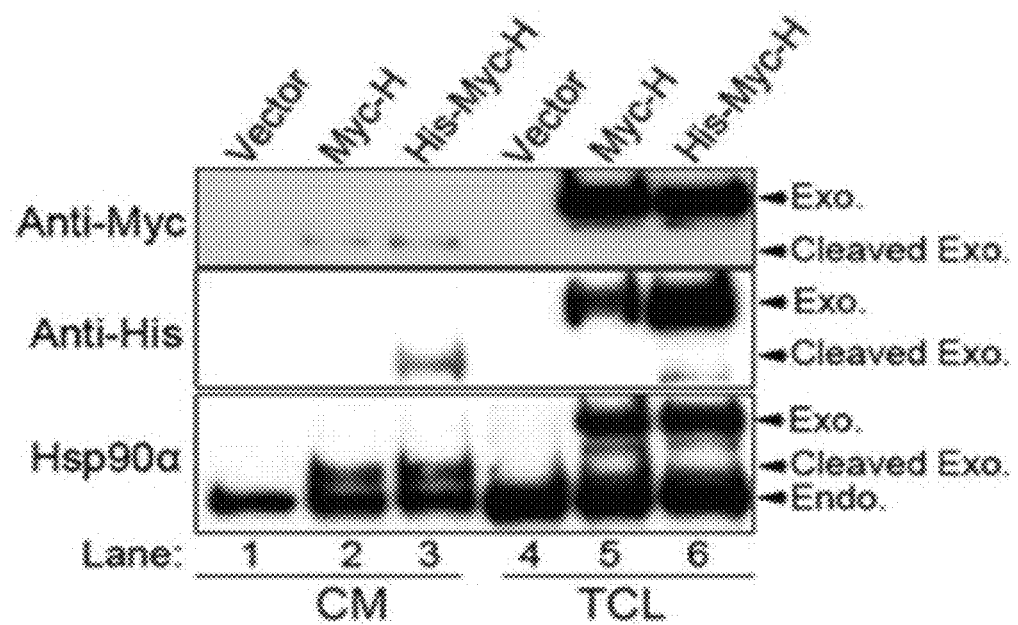
Figure 9:
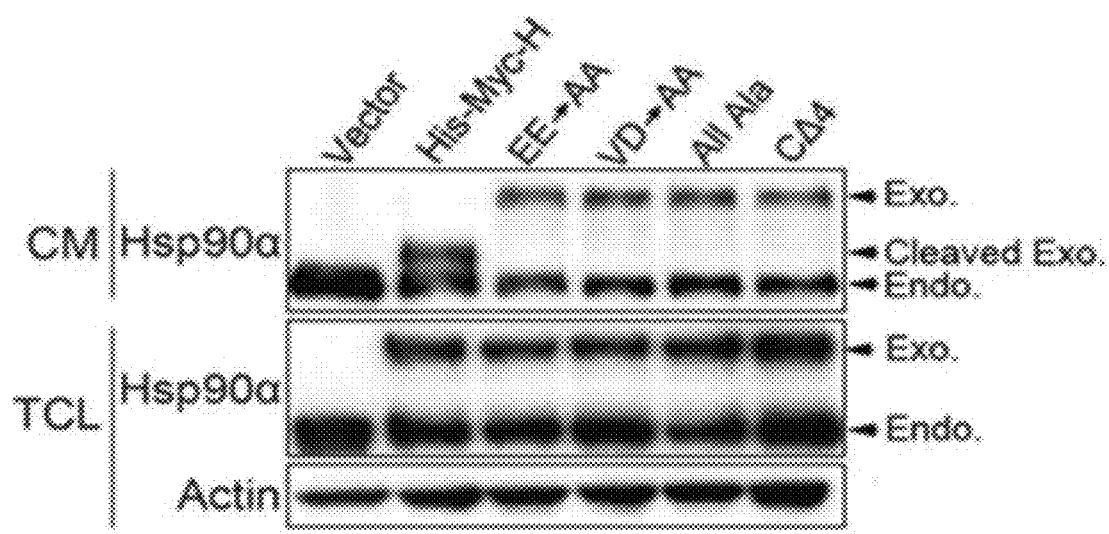

FIG. 9: The secreted Hsp90α by tumor cells is in a C-terminal truncated form.

Figure 10:
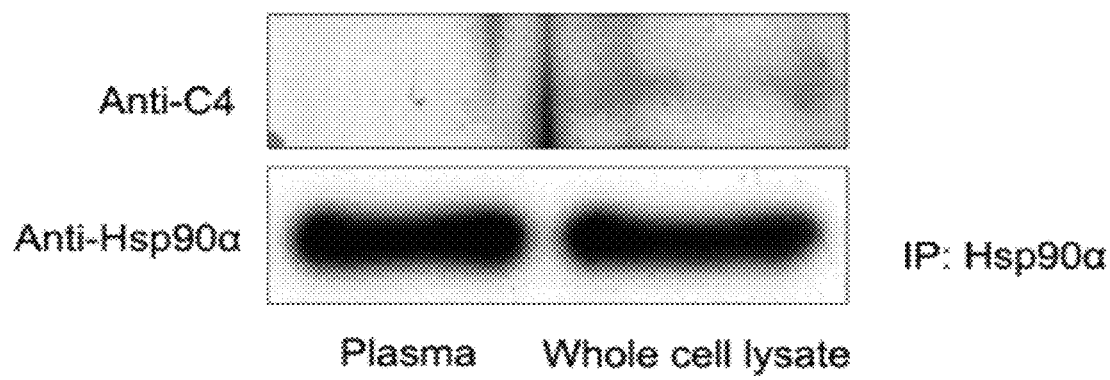

FIG. 10: The plasma Hsp90α lacks the C-terminal four amino acid residues.

Figure 11:
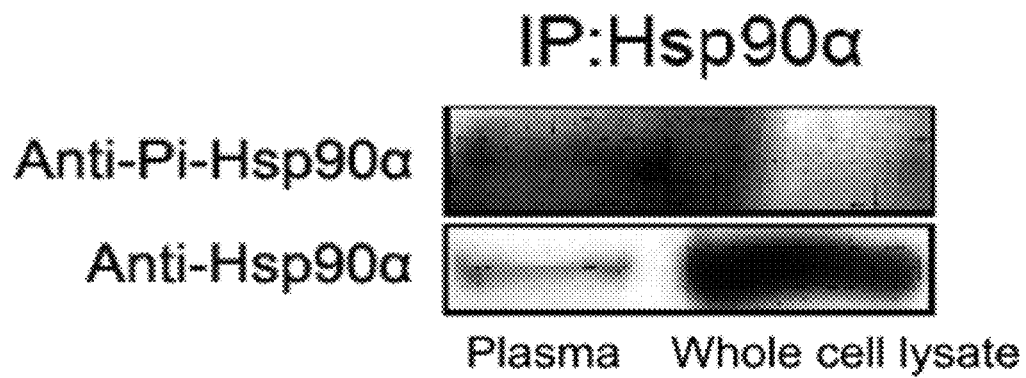

FIG. 11: The plasma Hsp90α is phosphorylated.

Figure 12:
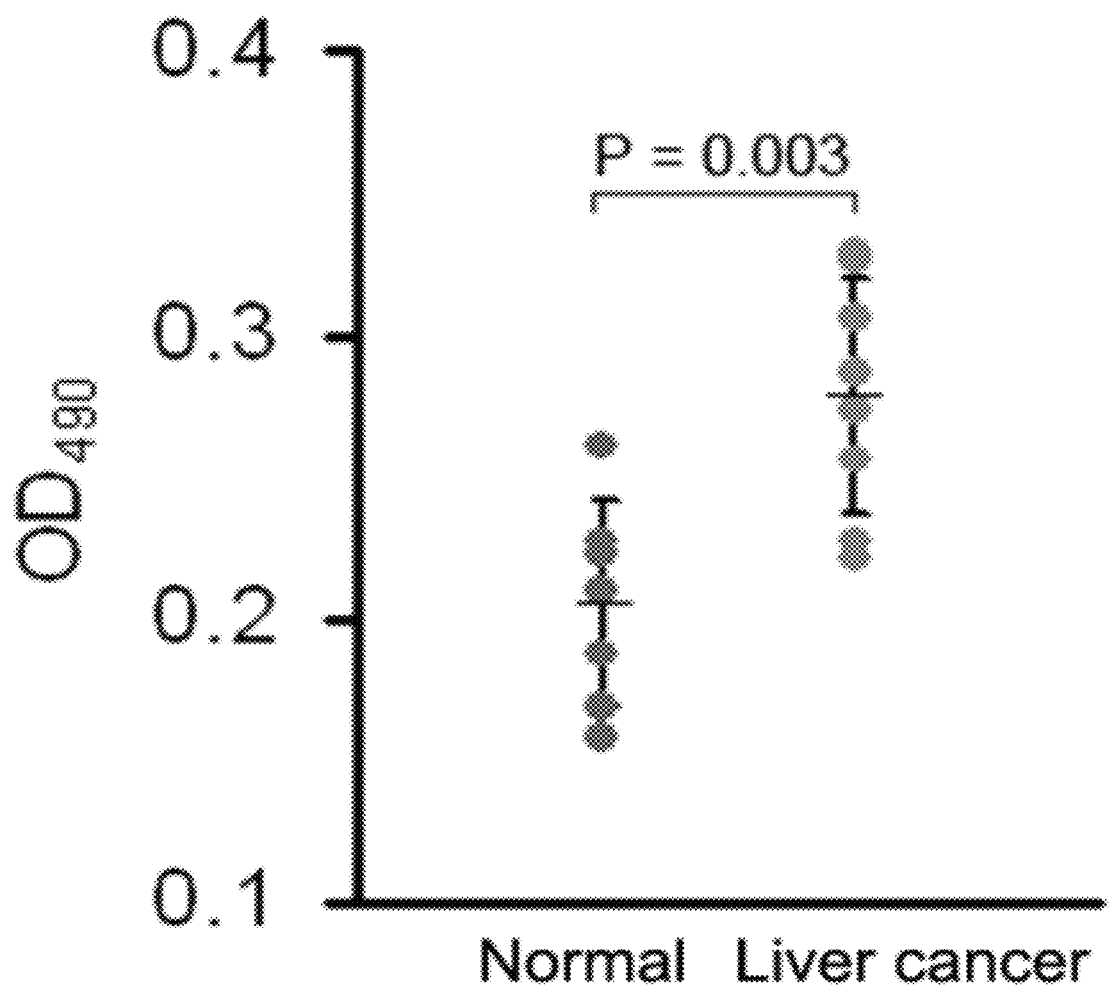

FIG. 12: The Thr90 phosphorylated Hsp90α level in the tumor patient plasma is elevated.

Figure 13:
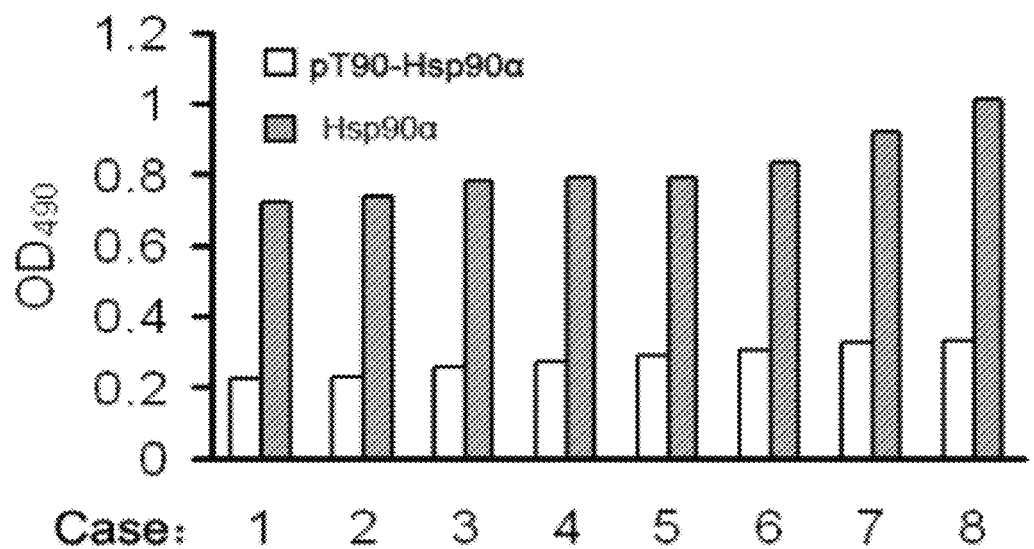

FIG. 13: In the plasma of tumor patient, the increment of Thr90 phosphorylated Hsp90α level is consistent with that of Hsp90α level.

Figure 14:
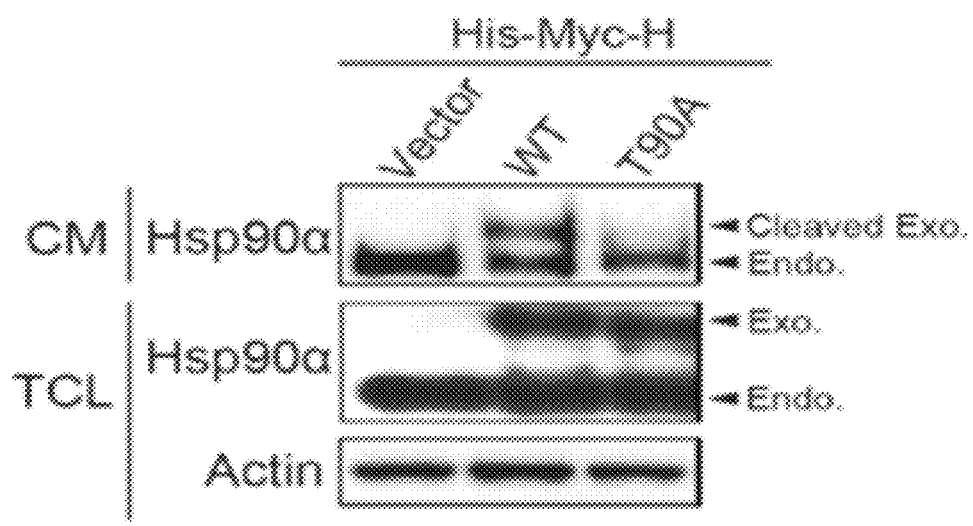

FIG. 14: Thr90 Phosphorylation of Hsp90α is a pre-requisite for Hsp90α secretion.

Figure 15:
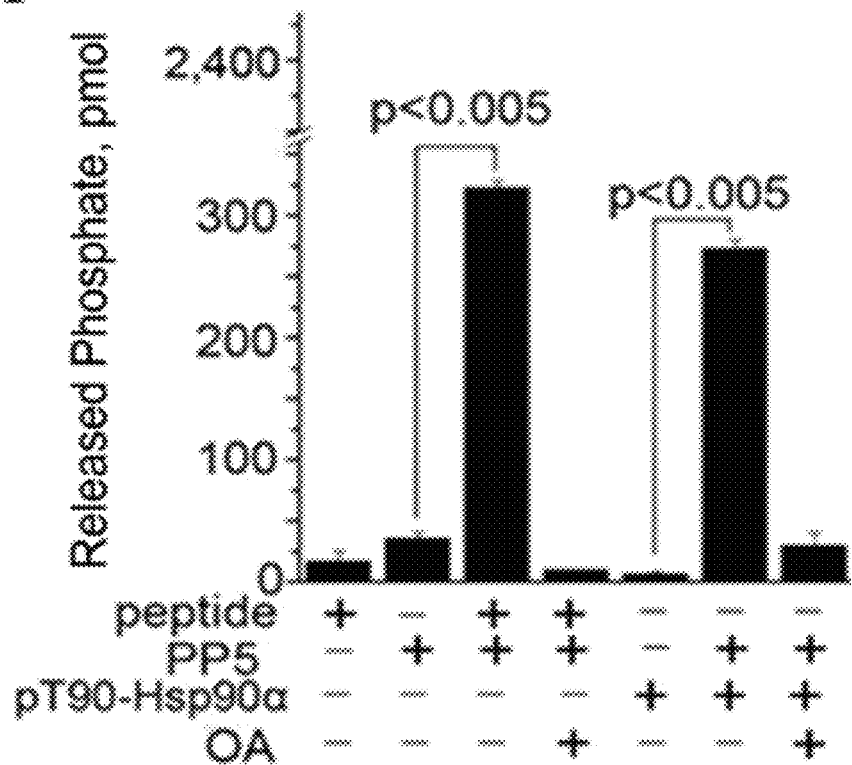
Figure 15:
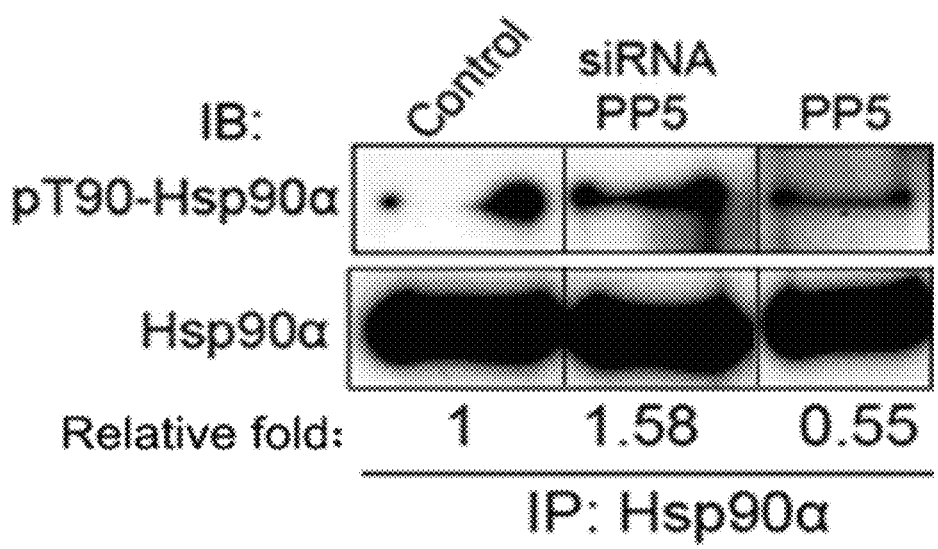

FIG. 15: PP5 dephosphorylates Thr90 phosphorylated Hsp90α.

A: Purified PP5 and Thr90 phosphorylated Hsp90α (pT90-Hsp90α) are incubated together, and the released free phosphate group is quantitatified. Peptide is a positive control. The result shows PP5 can directly dephosphorylate Thr90 phosphorylated Hsp90α.

B: In the human breast cancer cell line MCF-7, overexpression of human PP5 results in the inhibition of Hsp90αThr90 phosphorylation (0.55 of that in control group) and siRNA of endogenous human PP5 results in the increase of Hsp90αThr90 phosphorylation (1.58 of that in control group)

Figure 16:
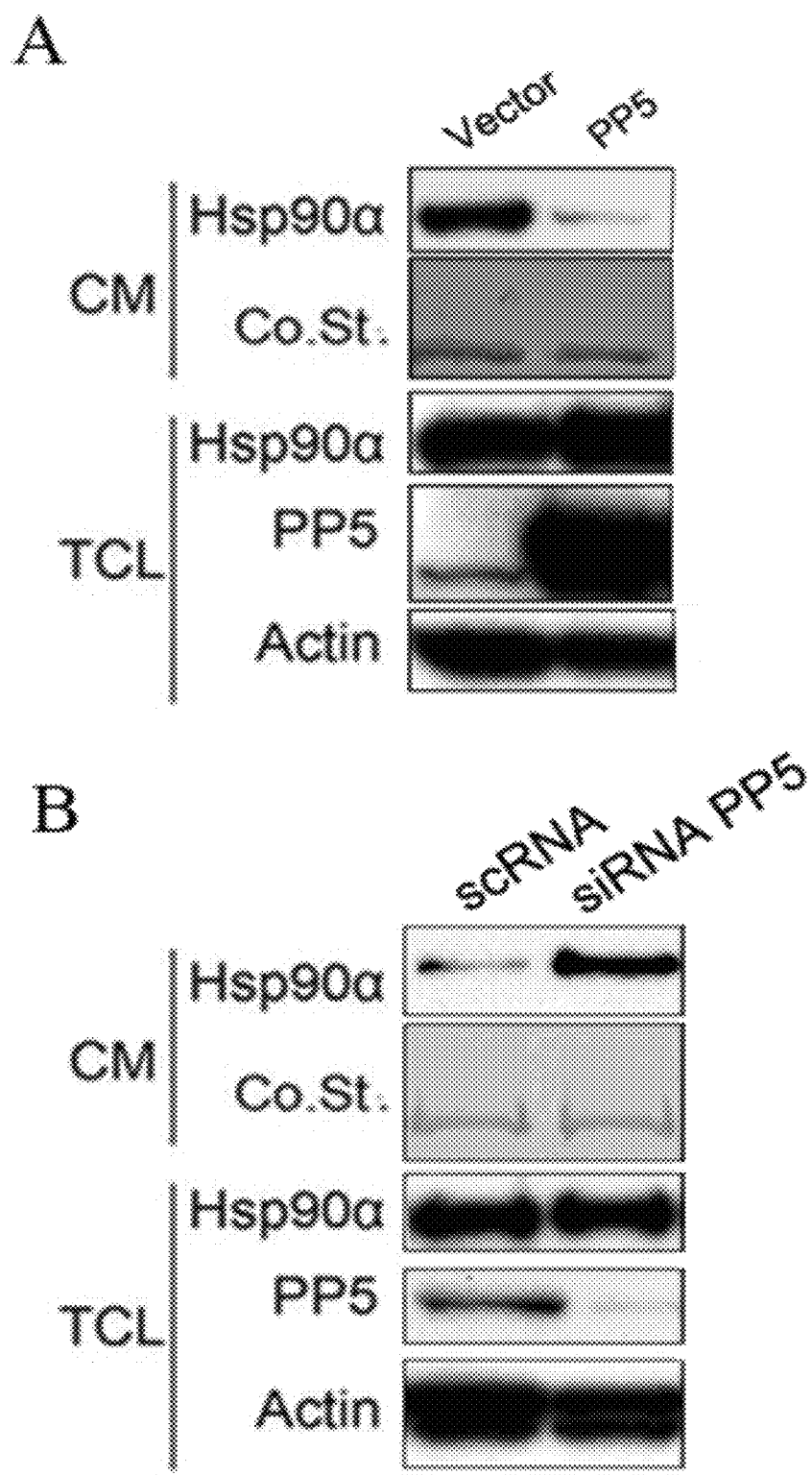

FIG. 16: PP5 regulates the secretion of Hsp90α.

A: In the human breast cancer cell line MCF-7, overexpression of human PP5 results in the inhibition of Hsp90α secretion.

B: In the human breast cancer cell line MCF-7, siRNA of endogenous human PP5 results in the increase of Hsp90α secretion.

Figure 17:
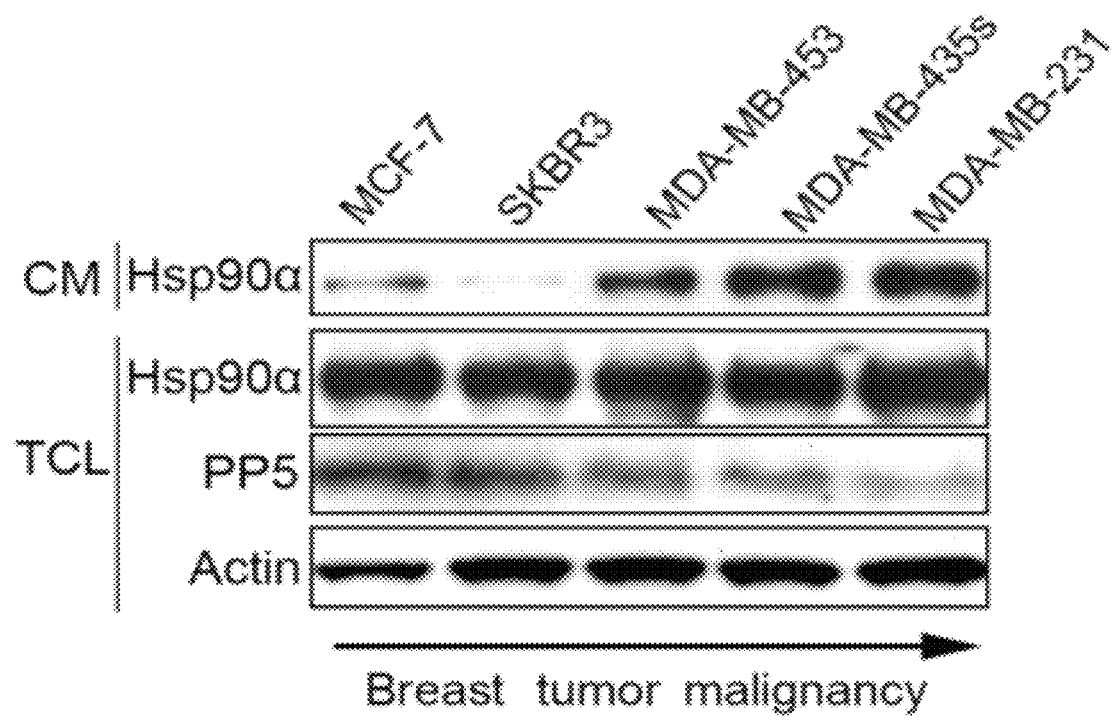

FIG. 17: The correlation of PP5 expression level and the secretion level of Hsp90α.

Figure 18:
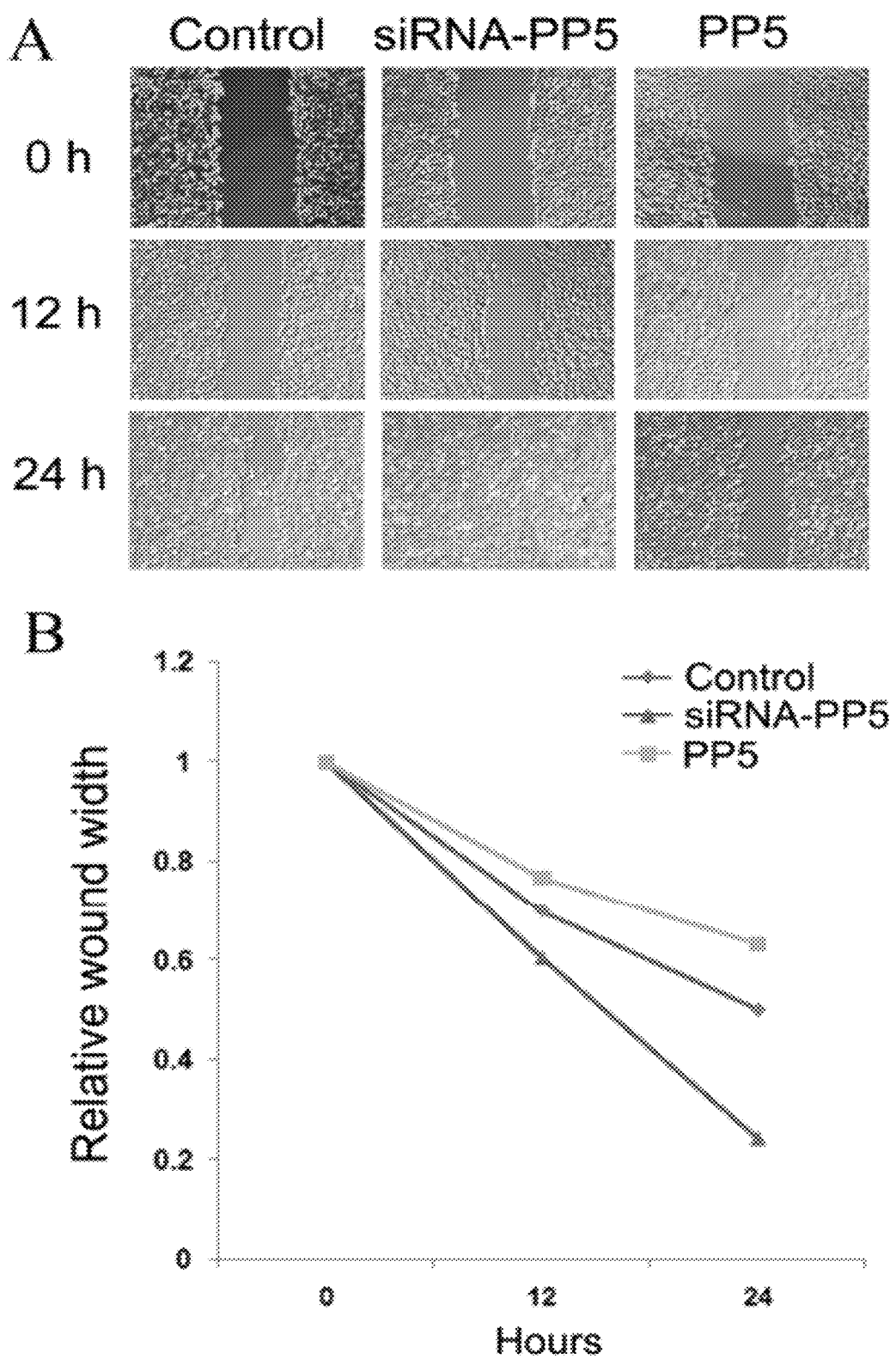

FIG. 18: The correlation of PP5 expression level and the invasive ability of the tumor cells.

Figure 19:
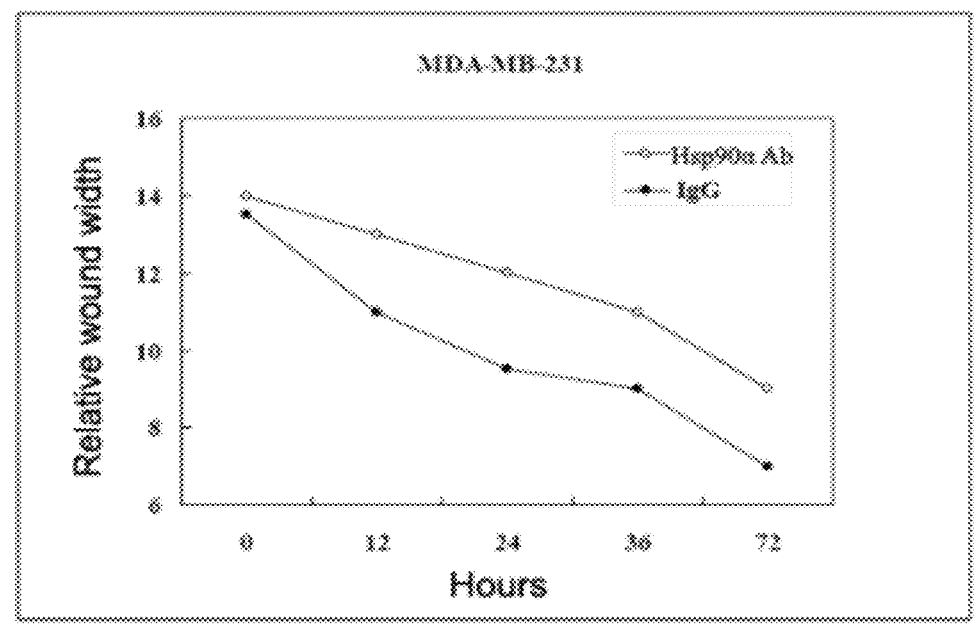
Figure 19:
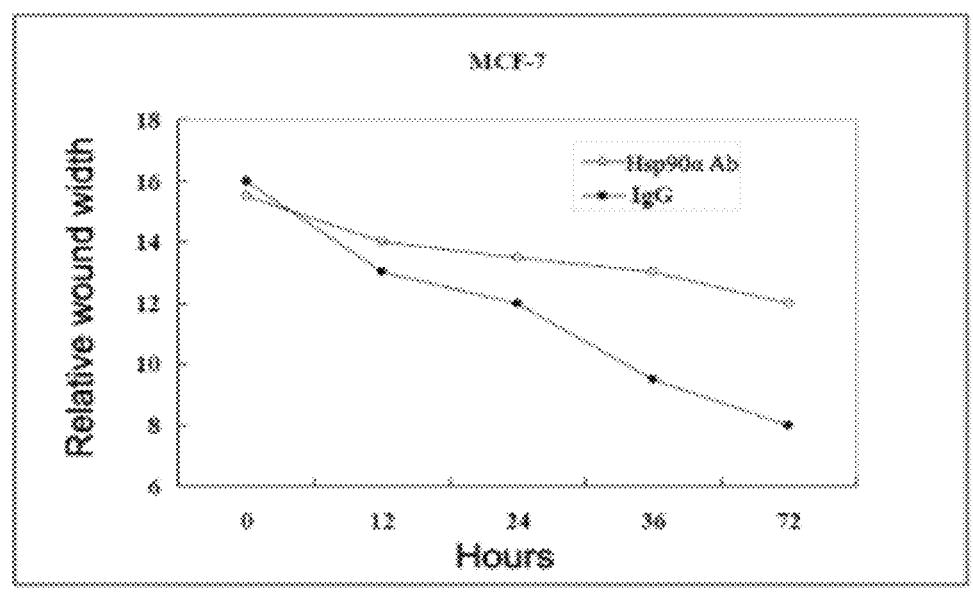

FIG. 19: The specific antibody of Hsp90α could inhibit the migration of tumor cells.

Figure 20:
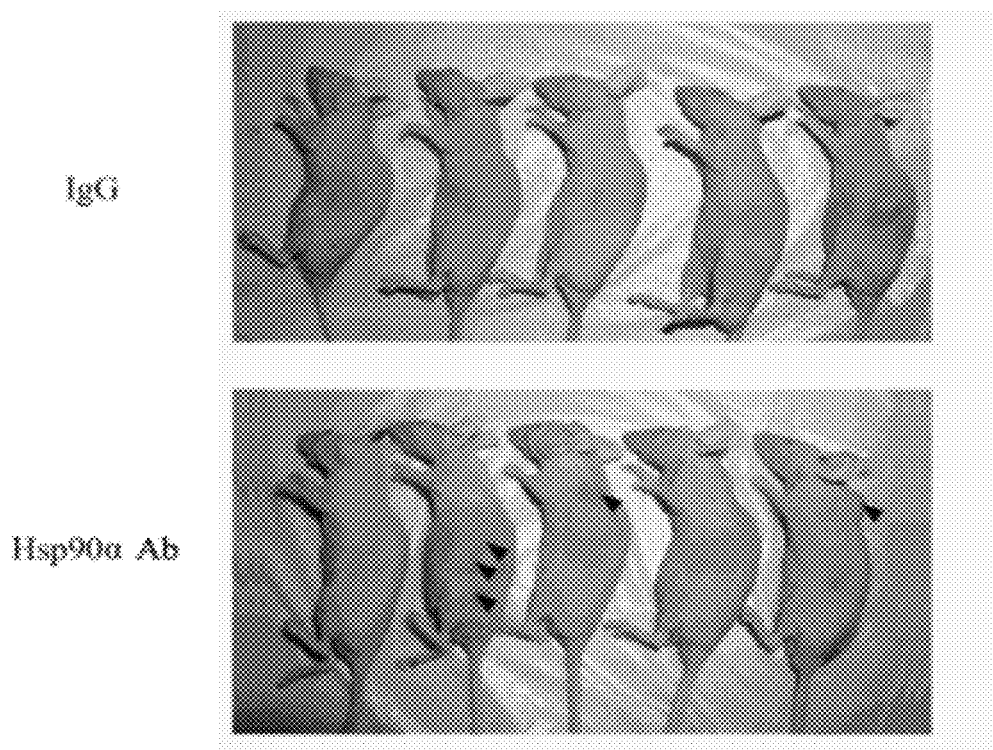
Figure 20:
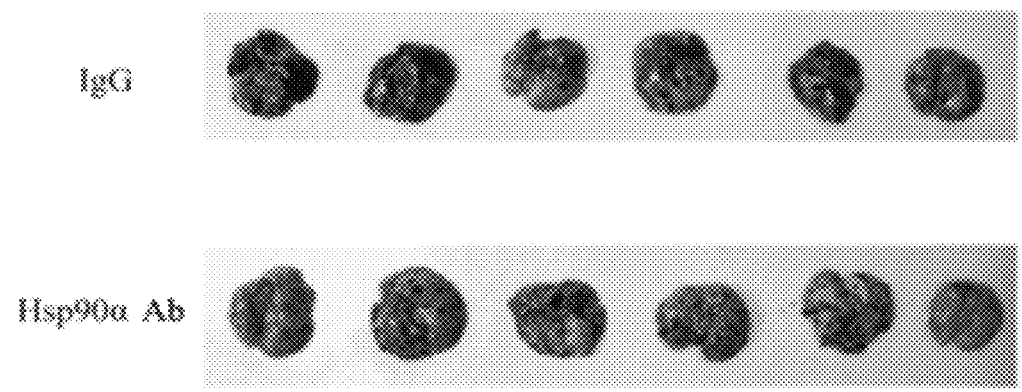

FIG. 20: The specific antibody of Hsp90α could inhibit tumor metastasis.

INFORMATION OF BIOLOGICAL MATERIAL DEPOSITION

Mouse hybridoma cell line SP2/0-Ag14 which produces monoclonal antibody E9 was deposited at China General Microbiological Culture Collection Center (CGMCC, Chinese Academy of Sciences Institute of Microbiology, Datun Road, Chaoyang District, Beijing) on Feb. 24, 2009 with the Deposition No. CGMCC No. 2903.

Mouse hybridoma cell line SP2/0-Ag14 which produces monoclonal antibody D10 was deposited at China General Microbiological Culture Collection Center (CGMCC, Chinese Academy of Sciences Institute of Microbiology, Datun Road, Chaoyang District, Beijing) on Feb. 24, 2009 with the Deposition No. CGMCC No. 2904.

DETAILED DESCRIPTION OF THE INVENTION

Carcinogenesis is caused by changes of certain intracellular signal transduction pathways, accompanied by changes of protein expression, modification and distribution. These changes could be used to monitoring of tumor development and progression, and these proteins are named as tumor marker. With the development of proteomics technology, it becomes possible to monitor the changes of tumor proteome qualitatively or quantitatively. So many new tumor markers have been found to provide more accurate and credible evidences for the tumor clinical diagnosis and prognosis.

This invention is based on a discovery of a novel blood tumor marker, i.e., plasma Hsp90α. Compared to intracellular Hsp90α (the amino acid sequence is SEQ ID No. 3, coding nucleic acid sequence is SEQ ID No. 4), the Hsp90α in plasma has a deletion of 4 amino acids in the C terminus.

Hence, in one aspect, this invention provides an isolated polypeptide, which is Hsp90α found in serum or plasma. In this application, the term "polypeptide of the invention" used herein refers to Hsp90α found in serum or plasma, which comprises or consists of the amino acid sequence of SEQ ID No. 1. Preferably, the term "polypeptide of the invention" used herein refers to the polypeptide consisting of the amino acid sequence of SEQ ID No. 1 sequence. In this application, the term "Hsp90α in plasma" or "Hsp90α in serum" can be used equally to refer to the protein Hsp90α in the blood but not intracellular or on cell surface. In this application, term "polypeptide" and "protein" can be used interchangeably.

The present invention also provides a polynucleotide encoding a polypeptide composing or consisting of the amino acid sequence of SEQ ID No. 1. In a specific embodiment, the polynucleotide comprises or consists of the amino acid sequence of SEQ ID No. 2.

The inventors also found that the polypeptide of the invention is in a phosphorylated form in plasma. Specifically, one or more amino acid residues in the amino acid sequence of SEQ ID No. 1 selected from the group consisting of Thr90, Ser231, Ser263, Tyr309 and a combination thereof are phosphorylated. Preferably, the Thr90 in the polypeptide of this invention is phosphorylated.

The special form of plasma Hsp90α(C-terminal truncated and phosphorylated) has not been described. Meanwhile, plasma Hsp90α also has never been reported to be related to tumor development and progression. EP1457499A1 describes the extracellular form of Hsp90α, and suggests that the inhibitors of Hsp90α can be used to treat tumor metastasis, to detect tumor invasiveness and to determine the dependence of tumor invasiveness on Hsp90α. However, the method described in EP1457499A1 is used to detect cell surface Hsp90α, but not related to plasma Hsp90α. Nor did EP1457499A1 disclose that plasma Hsp90α can be used to determine the degree and stage of malignancy, or to monitor the therapeutic response and prognosis of cancer by measuring the level of Hsp90α in plasma. WO/2008/070472 reported that the effects of the anti-cancer treatment targeting Hsp90α could be determined through detecting Hsp90α and its related factors in plasma, but it did not mention Hsp90α as an independent tumor marker in cancer diagnosis and prognosis.

The inventors examined the blood samples from nearly a hundred tumor patients (with breast cancer, liver cancer, pancreatic cancer, lung cancer and so on), and found that the level of Hsp90α in plasma is correlated to tumor malignancy, particularly metastasis; while the inflammatory response does not influence plasma level of Hsp90α. Therefore, plasma Hsp90α can serve as a tumor marker, which can be used for the diagnosis and prognosis of tumors and metastasis.

Additionally, the invention provides a kit examining the plasma levels of the polypeptide of the invention. The kit of the invention contains an agent capable of specifically binding to the polypeptide of the invention, which can be used to detect the level of plasma Hsp90α.

The invention also provides a method of detecting the level of plasma Hsp90α in a plasma sample of the subject by using an agent capable of specifically binding to said polypeptide. The method of the invention can be used to establish the diagnosis of carcinogenesis, malignancy and metastasis; to screening cancer in high-risk population; to determine the prognosis of cancer patients; and to determine the efficacy of surgery, radiotherapy or drug therapy.

As used herein, the term "an agent capable of specifically binding to a polypeptide of the invention" refers to molecules which can bind to the polypeptide of this invention with high-affinity. These agents also include molecules which can bind intracellular and cell surface Hsp90α. An agent capable of specifically binding to the polypeptide of the invention can be proteins, especially Hsp90α specific antibodies. In the preferred examples, the above antibody is a monoclonal antibody or antigen binding fragment, such as scFv, Fab, Fab 'and F (ab')2. In a specific embodiment, the antibodies are monoclonal antibody E9 or D10 which is produced by the cell line with deposition number of CGMCC No. 2903 or 2904, respectively.

Monoclonal antibodies are obtained by screening the cells which can secret the antibodies and then culturing the cells in vitro. The method is well known by the people in this field (Köhler G & Milstein C. (1975) Nature. 256, 495-7). The process for Hsp90α-specific monoclonal antibody preparation is as follows: for the first immunization, recombinant human Hsp90α (rhHsp90α, 100 μg) with Freund's complete adjuvant was injected subcutaneously on the back of BALB/c mice multi-pointly; 3 weeks later, same dose of rhHsp90α was injected intraperitoneal (i.p.) with Freund's incomplete adjuvant; the third immunization was administered by i.p. injection after 3 weeks with same dose (5 to 7 days later the blood titer was tested); the other 3 weeks later, 200 μg rhHsp90α was administered for the booster immunization by intraperitoneal injection. 3 days later, spleen cells were fused with hybridoma SP2/0-Ag14 (SP2/0) (Source: ATCC, number: CRL-1581) using HAT for screening. Then hybridoma cells were limited diluted. immune blot and ELISA methods were used to identify and eventually to select cell lines that can secrete specific Hsp90α antibodies.

According to the invention, the antibodies used for the preparation of the method or kit can specifically bind to Hsp90α, and preferably to Hsp90α in plasma. In an preferred embodiment, the antibodies specifically bind to Hsp90α with one or more following amino acid residues are phosphorylated: Thr90, Ser231, Ser263, Tyr309 and the combination thereof. In the preferred embodiment, antibodies described herein can specifically bind to Hsp90α with phosphorylated Thr90.

The invention also provides a method for detecting the level of plasma polypeptide. The level of plasma Hsp90α can be detected by any suitable methods. The methods described here include both direct and indirect means for detecting the polypeptide which can be used for the diagnosis of tumor development, malignancy and metastasis.

Direct measurements include methods of detecting the described polypeptide of the invention using its an agent capable of specifically binding to said polypeptide, for example using specific antibodies of the polypeptides by Western blot or ELISA.

The concentration of Hsp90α can also be indirectly determined by detecting the activity of Hsp90α. An example is the assay of thermal induced denaturation of luciferase, which can be used to detect the chaperone activity of Hsp90α (Johnson et al. (2000) J. Biol. Chem., 275, 32499-32507).

Preferably, the level of plasma Hsp90α can be detected by ELISA or Western blot, comprising the steps as follows:
a) collecting the whole blood of cancer patients, and obtaining plasma or serum by centrifugation;
b) using ELISA or Western blot to detect the Hsp90α level of plasma or serum obtained from the step a), in which plasma of healthy people is used as the negative control, while plasma of patients with malignant tumors is used as the positive control, optionally generating an Hsp90α concentration standard curve;
c) determining the tumor malignancy and stage according to the level of plasma Hsp90α, thereby determining tumor diagnosis, prognosis or efficacy of treatment.

In step b) other methods can also be used, such as methods based on antigen-antibody reactions as well as methods based on other principles directly or indirectly reflecting the concentrations of Hsp90α, for example the examination of the concentration of Hsp90α by detecting the activity of Hsp90α.

Standard Hsp90α used for the standard curve of ELISA is purified from the plasma of cancer patients and can also be obtained by recombinant construction, including the full length Hsp90α, fragments, and other recombinant proteins or conjugates containing the sequence of the Hsp90α. "the standard curve of Hsp90α concentration" refers to the correlation curve between Hsp90α concentration and absorbance values detected in the ELISA using standard Hsp90α samples. "Hsp90α standard" refers to the plasma Hsp90α protein, recombinant Hsp90α protein, fragments and derivatives with the purity of more than 95%.

"Determining the malignancy of tumor" refers to making a judgment of tumor malignancy by examining the Hsp90α concentration in the plasma samples of patients and comparing this value with negative and positive controls.

Both sandwich and competitive ELISA can be used to detect the level of Hsp90α in plasma. The competitive ELISA with higher sensitivity is preferred.

The general steps of Sandwich ELISA include: a) immobilizing a specific antibody onto a solid support, and removing the unbound antibodies and impurities by one or more washing steps; b) adding samples to be tested and incubating for a period of time, allowing the antigen in the samples to bind to the antibody immobilized on the solid support and form solid-phase antigen-antibody immune complexes, then removing the unbound substances; c) adding an enzyme-conjugated-antibody which can bind to the antigen in the solid phase immune complexes, and then removing the unbound enzyme-conjugated-antibody by thorough washes (the amounts of enzyme-conjugated-antibody bound to the solid support are positively correlated to the amount of antigen); and d) adding substrate and quantifying the amount of antigen according to the color reaction.

The general steps of competitive ELISA include: a) immobilizing a specific antibody onto a solid support and washing thoroughly; b) adding the mixture of the sample to be tested and a certain amount of enzyme-conjugated-antigen, and incubating for enough time and wash thoroughly. (If there is no antigen in the sample, the enzyme-conjugated-antigen can bind to the solid phase antibody without competition. If there are antigens in the sample, then the antigens in the sample compete with the enzyme-labeled-antigens to bind the immobilized antibody, and the amount of enzyme-labeled-antigen bound to immobilized antibody decreases. As a control, the reference tubes only contain the enzyme-labeled antigen); c) adding substrate and obtaining the absorbance value for each tube. The value of the reference tube is highest, and the difference between the reference tube and the sample tube represents the amount of antigens in the sample. The lighter the color is, the more antigens the sample contains.

If Sandwich ELISA is used, the antibodies are two different species of plasma Hsp90α specific antibodies. The immobilized antibody can be a rabbit polyclonal antibody with strong binding capacities, while the detection antibody is a mouse monoclonal antibody with high specificity. These two antibodies should have no cross-reaction.

If competitive ELISA is used, the antibodies should be the specific antibodies against plasma Hsp90α, which should have strong binding capacities and high specificity to both the competitive substance and Hsp90α.

If competitive ELISA is used, the competitive substances can be a labeled plasma Hsp90α standard protein. And the labeling does not interfere with the binding of Hsp90α standard protein to its antibody.

If Western blot method is used, the first antibody used is a specific antibody against plasma Hsp90α; the secondary antibody can be conjugated with horseradish peroxidase, or alkaline phosphotase; the substrate can be DAB or fluorescent substrate. The fluorescence substrate with high sensitivity is preferred.

The sensitivity of above methods should be 10 ng/ml or more sensitive.

The antibody specific for plasma Hsp90α used in this present invention can be a whole antibody, or its fragments and derivatives.

The antibodies of this invention can also be replaced by other agents capable of specifically binding to Hsp90α, wherein the agents include small molecule compounds, peptides and their derivatives.

The competitive plasma Hsp90α standard proteins can be labeled by biotin and various fluorescent labeling reagents. Biotin is preferred.

The cancers which can be detected by the kit or method described in this invention include, but are not limited to, lung cancer, liver cancer, gastric cancer, esophageal cancer, osteosarcoma, pancreatic cancer, lymphoma, colon cancer, breast cancer, prostate cancer, oral cancer, nasopharyngeal cancer, cervical cancer, leukemia, malignant melanoma, sarcoma, renal cancer, cholangiocarcinoma. "Tumor and its malignancy" refers to whether the tumor is benign, malignant, or metastasis.

The inventors demonstrated that, the plasma Hsp90α level in non-cancer human is 2-50 ng/ml, most in the range of 2-10 ng/ml. The level of plasma Hsp90α in patients diagnosed with cancer is higher than the normal level, while the plasma Hsp90α level in the patients having cancer metastasis is higher than 50 ng/ml, mostly higher than 200 ng/ml. This makes the plasma Hsp90α a new tumor marker, which would be helpful for the diagnosis of cancer, especially metastasis.

Thus, in an embodiment, the kit or method of this invention can be used to determine the existence of tumor, especially malignant tumors and tumor metastasis. To this end, the kit or method of this invention can be used to measure the Hsp90α level of plasma samples from potential tumor patients or potential tumor metastasis patients, and optionally compared with normal controls, and then determine the possibility of patients with tumor or tumor metastasis according to the Hsp90α level in the sample. The elevated Hsp90α level in plasma suggests higher possibility that the patients have suffered from malignant tumor, and for patients with known cancer, an elevated Hsp90α level strongly suggests possibility of tumor metastasis.

In another embodiment, the kit or method of the invention can be used to detect the level of plasma Hsp90α so as to screen high-risk populations. To this end, the kit or method of the invention can be used to detect plasma Hsp90α level in samples from high-risk populations, and optionally compared with normal controls, and then one can determine whether an individual within the population may have tumor according to the level of the sample. Elevated Hsp90α level indicates the higher possibility of the presence of a malignant tumor. It is well-known for the people in this field how to determine different high-risk groups depending on the type of cancer to be screened, individual factors such as age, family history, lifestyle, work environment, history of exposure to harmful compounds and so on. For example, patients having chronic hepatitis B or hepatitis C are at high risk of HCC.

In another embodiment, the kit or method of the invention can be used to detect the level of plasma Hsp90α to predict the prognosis of cancer patients. To this end, the kit or method of this invention can be used to detect plasma Hsp90α level in samples from cancer patients, and optionally compared with normal controls, and then one can determine the prognosis of cancer patients according to the level of Hsp90α in plasma samples. The maintenance of Hsp90α in a high level or further increase may relate to the poor prognosis. Therefore, the clinicians can be alerted to provide more closely observation to the patients, and if necessary, change the current treatment.

In another embodiment, the kit or method of the invention can be used to detect the plasma level of Hsp90α, which is thus used to determine whether the treatment such as the surgery, radiotherapy or chemotherapy on cancer patients is effective. To this end, the kit or method of this invention can be used to detect plasma Hsp90α level in samples from cancer patients, and optionally compared with normal controls, and then one can determine the prognosis of cancer patients according to the level of Hsp90α in plasma samples. According to the level of the Hsp90α, one can determine whether the surgery, radiotherapy or chemotherapy on cancer patients is effective and/or whether the treatment should be continued.

The inventors further demonstrated that the Hsp90α in plasma is secreted by tumor cells and is different from that within the tumor cells. Therefore, it is assumed that the tumor development and metastasis may be suppressed by inhibiting the secretion of Hsp90α into plasma. This point was demonstrated by the mouse tumor metastasis model using the specific antibody against plasma Hsp90α. Therefore, the secretion of Hsp90α can be used as a new target for screening new anticancer drugs.

In another aspect, the invention provides a method for preventing or treating tumor metastasis comprising administering to a cancer patient an inhibitor of the polypeptide of the invention.

According to one embodiment of this invention, the aforementioned inhibitor is a specific antibody of the polypeptide. Preferably, the antibody is a humanized antibody or its fragments. In one embodiment, these antibodies specifically bind to a phosphorylated form of the polypeptide of the invention, said phosphorylated form of the polypeptide contains one or more phosphorylated amino acid residues in the amino acid sequence of SEQ ID No. 1 selected from the group consisting of Thr90, Ser231, Ser263, Tyr309 and a combination thereof. In a preferred embodiment, the antibody can bind to the polypeptide phosphorylated at Thr90. In one specific embodiment, the antibody is MAb E9 or D10 which is produced by the cell line deposited under CGMCC No. 2903 or 2904, respectively. As demonstrated herein, these antibodies can completely inhibit the lymph node metastasis of tumors in mouse model and can inhibit the lung metastasis to an extent up to 56%.

So, in another aspect, this invention also relates to an antibody specifically binds to the Hsp90α in blood. In a specific embodiment, the antibody is MAb E9 or D10 which is produced by the cell line deposited under CGMCC No. 2903 or 2904, respectively. Preferably, the antibody is a humanized antibody or an antigen binding fragment thereof. In a specific embodiment, the antibody specifically binds to a phosphorylated form of the polypeptide of the invention, said phosphorylated form of the polypeptide contains one or more phosphorylated amino acid residues in the amino acid sequence of SEQ ID No. 1 selected from the group consisting of Thr90, Ser231, Ser263, Tyr309 and a combination thereof. In one preferred embodiment, the antibody specifically binds to the polypeptide phosphorylated at Thr90. Preferably, the antibody inhibits tumor growth, especially metastasis. This invention also related to a conjugate comprising the antibody and a diagnosis or treatment moiety. For example, the diagnosis moiety is a fluorophore, while the treatment moiety is a chemotherapeutic agent.

The inventor also found the amount of Hsp90α secreted by tumor cells is related to the level of Protein phosphatase 5 (PP5). In benign tumor, secreted Hsp90α is low but PP5 expression level is high. In malignant tumor, secreted Hsp90α is high but PP5 expression level is low. Therefore, the level of secreted Hsp90α is negatively interrelated with the level of PP5. As a result, by detecting the expression level of PP5, it is possible to predict the amount of secreted Hsp90α.

The inventors also found that the secretion of Hsp90α can be inhibited by cellular PP5. Over-expression of a nucleic acid molecule encoding PP5 in the cell can inhibit Hsp90α secretion, while a decrease in the expression level of PP5 will result in an increase in Hsp90α secretion. So by over expressing PP5, Hsp90α secretion can be inhibited and the tumor progression and metastasis may be inhibited. According to our experiment, we found that over expression of PP5 inhibits the metastasis of MCF-7. So PP5 can be a new therapeutic target for tumor treatment.

So, in a further aspect, this invention provides a method for inhibiting tumor invasiveness and metastasis, wherein a step of inhibiting the phosphorylation of Hsp90α within tumor cells. In one embodiment, this method comprises a step of inhibiting Thr90 phosphorylation of Hsp90α in tumor cells. In one specific embodiment, this method comprises a step of over-expressing a nucleic acid molecule encoding PP5 in tumor cells. Preferably, the over-expression of PP5 is achieved by the means of gene introduction. In one embodiment, this method comprises a step of over-expressing a nucleic acid molecule encoding PP5 having an amino acid sequence of SEQ ID No. 5. In one specific embodiment, the nucleic acid molecule comprises the nucleotide sequence of SEQ ID No. 6. This invention also provides a method of inhibiting the phosphorylation of Hsp90α in tumor cells comprising a step of over-expressing PP5 in tumor cells using a vector carrying a polynucleotide encoding PP5 operably linked to a promoter. The method can be used to inhibit tumor invasiveness and metastasis.

This invention also provides methods and models for screening for anti-tumor drugs by using plasma Hsp90α and its derivatives. Such anti-tumor drugs includes, but not limited to, plasma Hsp90α binding proteins, small peptides, and small compounds as well as inhibitors which can suppress the activity of plasma Hsp90α.

EXAMPLES

Example 1

The Collection and Preparation of Mouse Plasma Samples, and the Detection of Plasma Hsp90α

Figure 1:
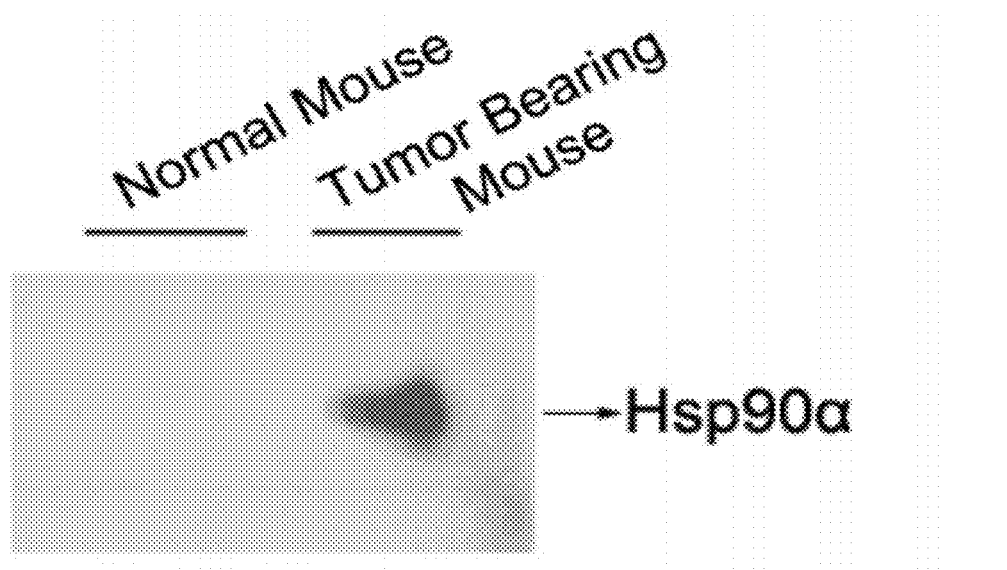
FIG. 1: The plasma Hsp90α level in tumor-bearing mice is significantly increased than in that in normal mice.

Balb/c mice with average body weight of 20 gram (purchased from Beijing Vital River Laboratory Animal Technology Co., Ltd.) were randomized divided into two groups, 3 for each. The mice of experiment group were inoculated with $10^6$ H22 (CCTCC ID: GDC091) cells, while the mice in control group were not inoculated. When the diameter of tumor reached about 2 cm (about 20 days), blood was collected from eye down veniplex. Anticoagulant was added and hemolysis was prevented. If hemolysis occurred, the blood would be recollected. The blood sample was centrifuged at 4° C. with 6000 g for twice, and supernatant was saved. The amount of plasma Hsp90α was detected by Western blotting using Rabbit anti-human Hsp90α pAb (Labvasion). BCA method was used to determine the total amount of proteins in samples, which ensured that the loading amounts of different samples were equal. The result is shown in FIG. 1. Compared to control mice, the plasma Hsp90α was elevated in tumor bearing mice.

Example 2

The Collection and Preparation of Plasma Samples from Normal People and Tumor Patients, and the Detection of Plasma Hsp90α

The blood of normal people and cancer patients were collected and delivered to lab within 24 hours at 4° C. If hemolysis occurred, the samples should be recollected. The samples were centrifuged at 4° C., 6000 g twice and supernatant was saved. The amount of Hsp90α was determined by Western blotting. If the samples could not be examined immediately, the samples should be stored at –80° C. By comparing the results with clinical diagnosis, the correlation between Hsp90α and tumor malignancy was confirmed.

Figure 2:
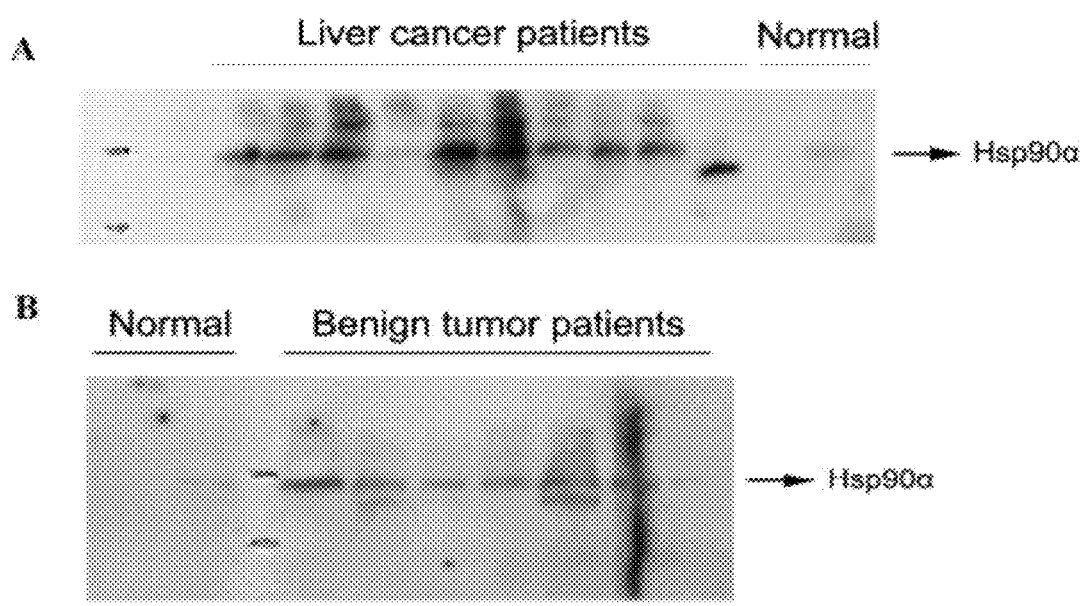
FIG. 2: The plasma Hsp90α level in cancer patients is significantly increased compared with that in normal people.

The protocol for Western blotting: the plasma samples were mixed 1:1 with loading buffer. 1-2 µl sample is loaded for SDS-PAGE. Primary antibody is the one which can specifically recognize plasma Hsp90α(rat mAb SPA-840, Stressgen). The aecondary antibody is goat anti-rat antibody conjugated with HRP (purchased from Zhongshanjinqiao). As the result shows in FIG. 2, the amount of Hsp90α in HCC patients is 10-fold higher than that of normal people (A), while it is elevated by 2-fold in benign galactocele and hysteromyoma patients compared with that of normal people.

Example 3

Preparation of Rabbit pAb and Mouse mAb Against Hsp90α

Primers with the following sequences were used to clone the gene of Hsp90α:

```
Hsp90α-Sal1-Re:
ACGCGTCGACTTAGTCTACTTCTTCCATGC      (SEQ ID No. 8)
and

Hsp90α-Sph1-For:
ACATGCATGCATGCCTGAGGAAAC CCAGACC.   (SEQ ID No. 9)
```

Primers were synthesized by Invitrogen. Pfu DNA polymerases (NEB) were used to amplify Hsp90α from human liver cDNA library (Stratagene). Sph1 and Sal1 (NEB) were used to digest the amplified PCR products and pQE80L vector (Qiagen). Then T4 ligases were used for ligation. The products were transformed into Top10 cells (Transgen) for amplification and validation. The validated plasmids were further transformed into BL21DE3 cells (Transgen) for expression. The recombinant Hsp90α proteins were purified by ion-exchange chromatography SP HP, pH6.8, collecting 10 ms/ml peak and Q HP, pH7.8, collecting 19 ms/ml peak.

Recombinant human Hsp90α with a purity higher than 95% was used to immune adult male New Zealand Rabbit by dorsal subcutaneous multi-point injection at 100 µg for each time. Two weeks later, the secondary immunization was conducted according to the same method, except that the amount of Hsp90α injection was reduced to 50 µg. Boost injections were conducted every 1 week after the secondary immunization for twice. The titer of antibody in serum was determined 7-10 days after the boost immunizations. Eight days after the last immunization, serum was collected and stored at –20° C. Affinity chromatography conjugated with antigen was used to purify the antibody from the serum. Purified rabbit pAb was named as S2.

BALB/C mice were immunized by recombinant human Hsp90α. Primary immunity: 100 µg antigen and Freund's complete adjuvant was injected dorsal subcutaneously multipoint. The second immunity was conducted 3 weeks later with Freund's incomplete adjuvant using the same dose and i.p. injection. The third immunization was operated 3 more weeks later without adjuvant (blood was collected for test after 5-7 days). Three more weeks later, 200 µg antigen was injected i.p. as the boost immunization. 3 days later, spleen cells were collected and fused with SP2/0-Ag14(SP2/0) hybridomas (ATCC: CRL-1581). HAT was used for the screening. Limited dilution was used to colonize hybridomas. Western blotting and ELISA were used for identification. Finally, E9 and D10, which secrete specific antibody against Hsp90α, were obtained and stored as CGMCC No. 2903 and 2904 on Feb. 24, 2009.

Figure 3:
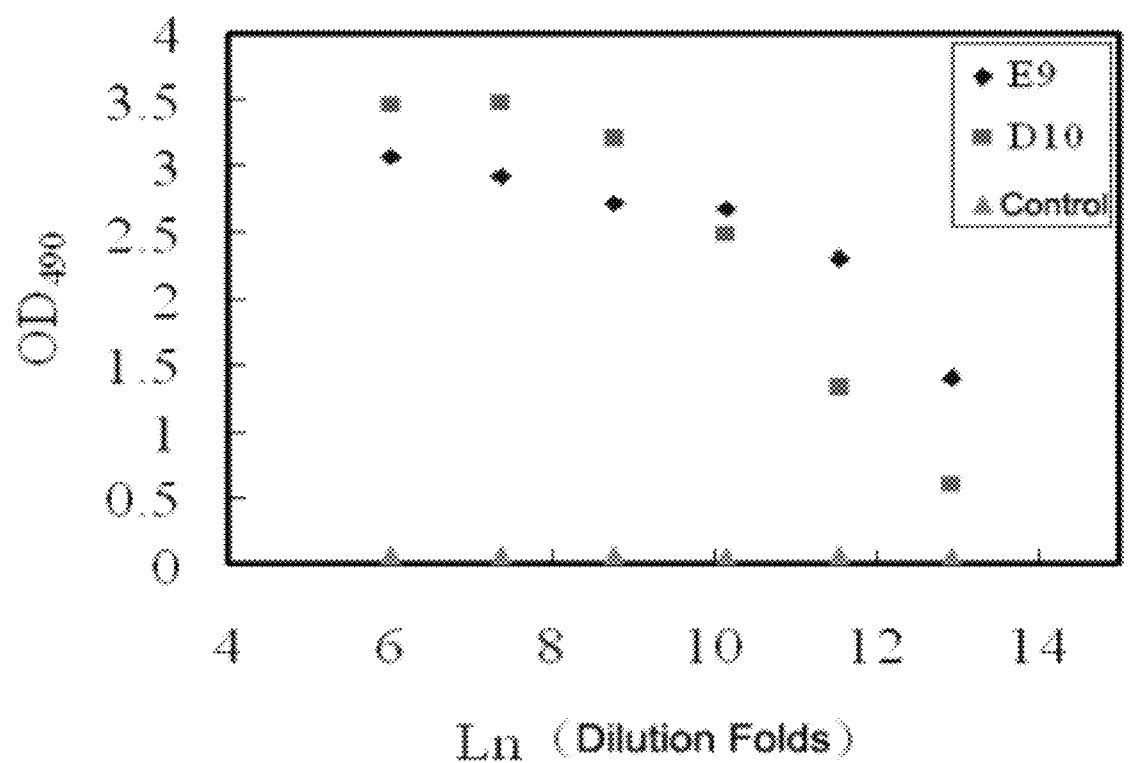
FIG. 3: The titer assay of the mouse monoclonal antibody of E9 and D10.

Indirect ELISA was used to determine the titers of E9 and D10. Shown as FIG. 3, the average titers of E9 and D10 respectively reaches 500,000, which is qualified to be used in the detection of plasma Hsp90α. Indirect ELISA: recombinant human Hsp90α was plated at 4° C. overnight with the concentration of 10 µg/ml. Then the plate was blocked at 37° C. for 1 hour. E9 or D10 with 1:400, 1:1600, 1:6400, 1:25600, 1:102400, 1:509600 dilutions was added and incubated for 2 hours at RT. Then goat anti-mouse antibody conjugated with HRP was added and incubated for 1 hour at room temperature, then o-phenylendiamine was added and absorbance at OD 490 nm was detected.

Example 4

Measurement of the Concentration of Hsp90α by E9, S2 and Sandwich ELISA

Figure 4:
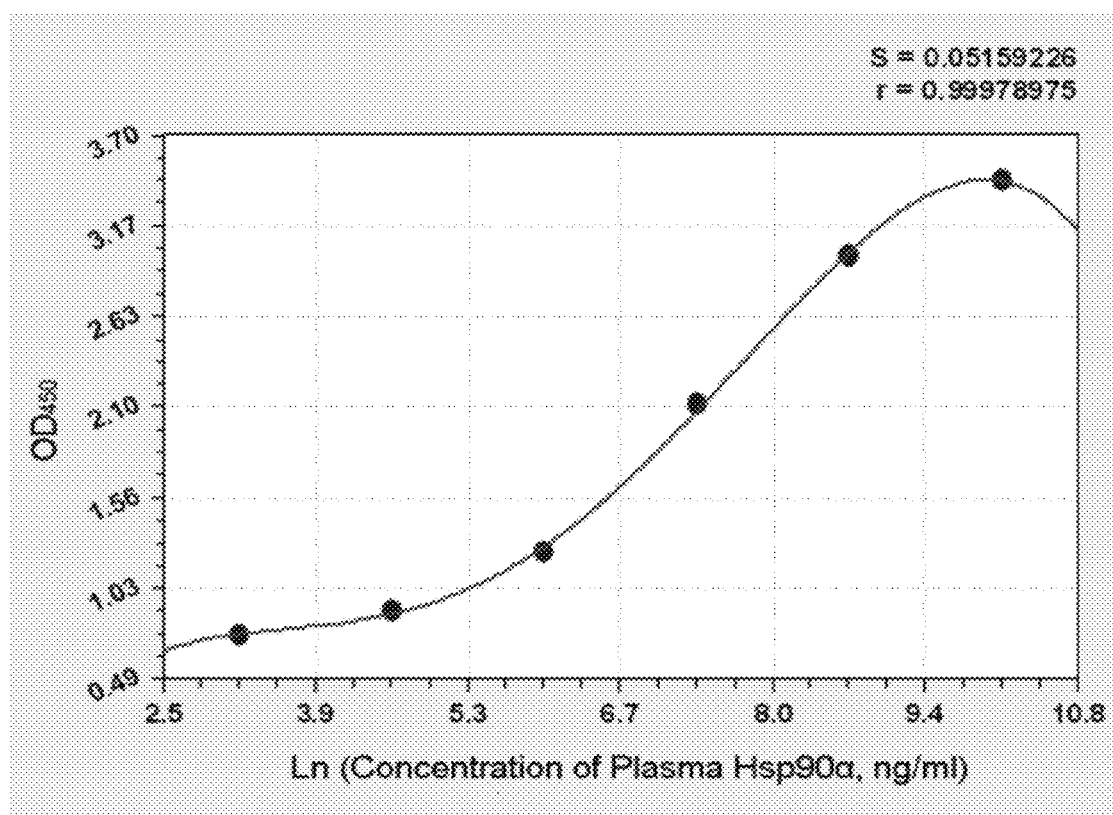
FIG. 4: The standard curve of plasma Hsp90α using mouse monoclonal antibody E9 and rabbit polyclonal antibody S2 (sandwich ELISA).

In the method of sandwich ELISA to test the concentration of plasma Hsp90α, two antibodies from distinct species were used. S2 with high binding capacity (the preparation of S2 was described in example 3) was used as the coating antibody and E9 (the preparation of E9 was described in example 3) with high binding specificity was used as the detecting antibody. There is no cross reaction between these two antibodies. The method is repeatable and sensitive. FIG. 4 shows that the sensitivity of this method is 5 ng/ml.

Example 5

The collection and Preparation of Human Plasma, the Detection of Plasma Hsp90α and Determination of Tumor Malignancy (Sandwich ELISA)

The blood of normal persons, cancer patients and inflammation patients was delivered to lab at low temperature within 24 hours. If hemolysis occurs, the blood should be re-collected. The samples were centrifuged at 4° C., 6000 g twice and supernatant was saved. The amount of plasma Hsp90α was determined by ELISA. The samples were stored at −80° C. if they were not examined immediately. By comparing the results with clinical diagnosis, the correlation between Hsp90α and tumor malignancy was confirmed.

Two different Hsp90α antibodies were used in sandwich ELISA. S2 was coated on the plate and incubated overnight at 4° C. The plate was blocked for 1 hour at 37° C. The samples were diluted by 10 folds and were added to the plate (100 μl/well). After 2 hours incubation at 37° C., E9 was added and incubated at 37° C. for 2 more hours. Goat anti-mouse antibody conjugated with HRP was added to incubate for another 1 hour. O-phenylendiamine was added and absorbance at OD490 nm was detected. The results were shown as FIGS. 5, 6 and 7. The standard curve comprises a serial of samples containing the gradient concentration of standard Hsp90α proteins and 10% of negative plasma in each sample, which was used to exclude the background of plasma.

Figure 5:
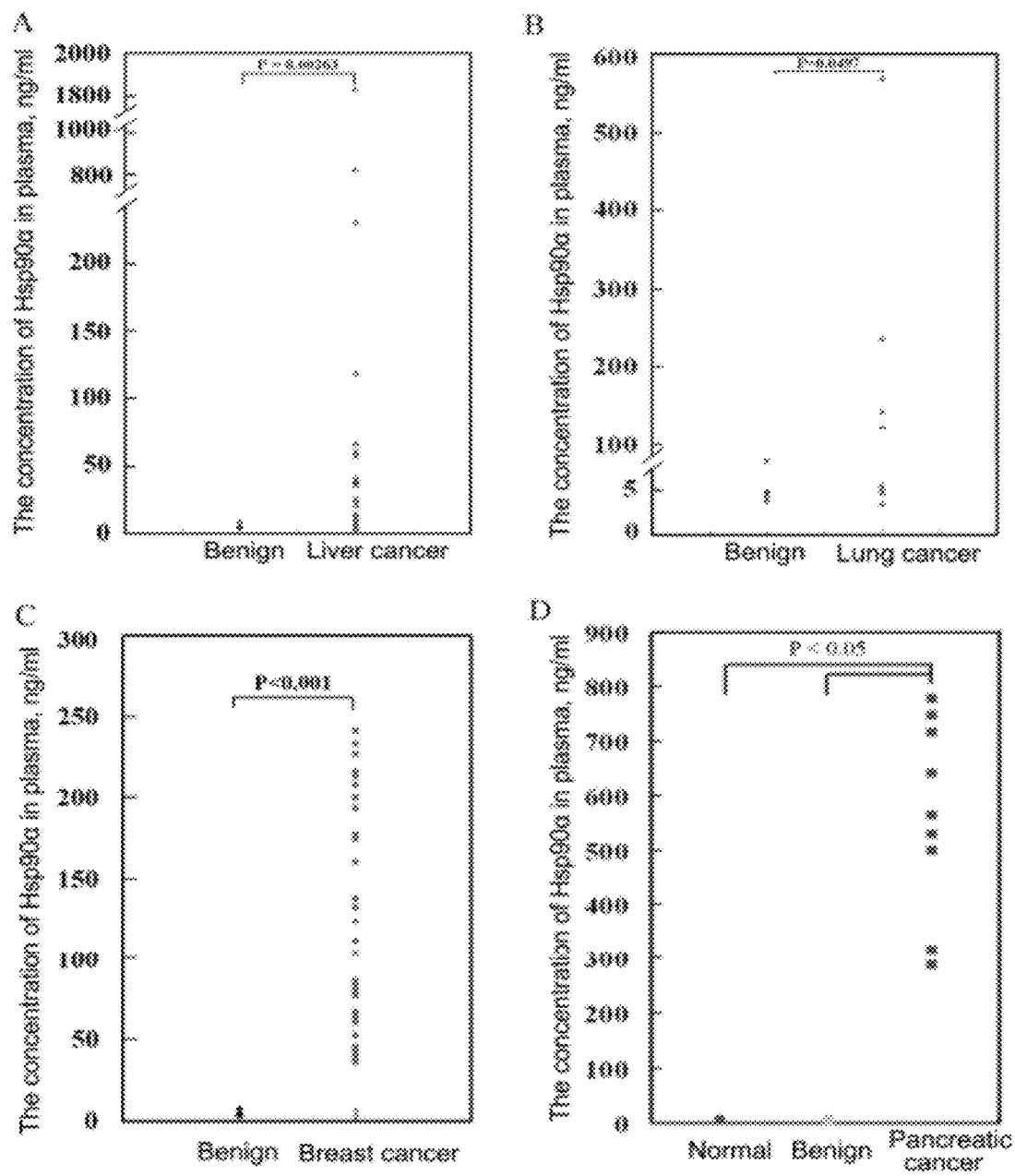
FIG. 5: Quantitative measurement of plasma Hsp90α level in lung, liver, pancreatic cancer patients as well as benign galactoma and myoma of uterus patients using sandwich ELISA.

As shown in FIG. 5, the amount of plasma Hsp90α in benign tumor patients (including benign galactocele and hysterromyoma patients, seven cases) is between 2-10 ng/ml, mainly in 2-5 ng/ml. 69% (20/29) liver cancer patients have plasma Hsp90α above 50 ng/ml, which is in average 10 folds higher than that of benign tumor patients, p=0.00263, student t test (A); 64% (9/14) lung cancer patients have plasma Hsp90α above 50 ng/ml. The average concentration is 10 folds higher than that of benign tumor patients, p=0.0497, student t test (B). 78% (25/32) breast cancer patients have plasma Hsp90α above 50 ng/ml. The average is 10 folds higher than that of benign tumor patients, p<0.001, student t test (C). 100% (10/10) pancreatic cancer patients have plasma Hsp90α above 50 ng/ml. The average is 10 folds higher than that of benign tumor patients, p<0.05, student t test (D).

As shown in FIG. 6, in liver cancer (17 cases, 7 metastasis) (A), lung cancer (10 cases, 2 metastasis) (B) and breast cancer (21 cases, 10 metastasis) (C) patients, the levels of Hsp90α in metastasis patients were significantly higher than those in patients without metastasis. Liver cancer p=0.003, breast cancer p=0.002, student t test.

As shown in FIG. 7, inflammation patients, including 10 pneumonia cases (A), 10 hepatitis cases (type A 5 cases, type B 5 cases) (B) have plasma Hsp90α between 2-10 ng/ml, which shows no significant difference when compared with that of normal persons (3 cases), p=0.2988, 0.5177, 0.138 by student t test, respectively.

The normal people's samples were collected from healthy volunteers, while tumor patients and inflammation patients' samples were collected from Beijing Cancer Hospital and Xiamen First Hospital.

Example 6

The Plasma Hsp90α was Secreted by Tumor Cells

Nude mice (purchased from Beijing Vital River Laboratory Animal Technology Co., Ltd.) with average body weight of 20 g were divided into two groups, 6 mice for each group. Each mouse was injected with $10^6$ Hela cells (ATCC: CCL-2). Control group were normal mice without tumor. When the diameter of tumor reached 2 cm (about 20 days), blood was collected from eye veniplex. Hsp90α antibody (rat mAb, Stressgen) that specifically recognizes human Hsp90α but not mouse Hsp90α was used to detect the plasma Hsp90α. As shown in FIG. 8, the plasma Hsp90α in the tumor-bearing mice is specifically recognized by human but not mouse Hsp90α antibody, which indicates that the plasma Hsp90α was secreted by the xenograft tumor cells.

Example 7

The Hsp90α Secreted by Rumor Cells was C-Terminally Truncated

Using Hsp90α-pc3.1-Nhe1-For-Myc: GCTAGCTAGCGCCACCATGGA ACAAAAACTCATCT-CAGAAGAGGATCTGCCTGAGGAAACCCA-GACCCAAGAC (SEQ ID No. 10) and Hsp90α-pc3.1-Xho1-Re-nostop: CCCGCTCGA GTGTCTACTTCTTCCATGCGTGATG (SEQ ID No. 12) as primers (synthesized by Invitrogen) and Pfu DNA polymerase (NEB) to amplify Hsp90α from the template of pQE80L-Hsp90α (obtained in example 3). The products were digested and inserted into pcDNA3.1/Myc-His(−) (Invitrogen) to obtain Hsp90α with Myc tag at the N terminus, which was named as Myc-H. Similarly, His-Myc-H with N-terminal tandem His-Myc tags was amplified by Hsp90α-pc3.1-Nhe1-For-His-Myc: GCTAGCTAGCGCCACCATGCATCAT-CATCATCATCATGAACAAAAACTCATCTCAGA AGAGGATCTGCCTGAGGAAACCCAGACCCAAGAC (SEQ ID No. 11) and SEQ ID No. 12 primers. These two plasmids were transiently transfected into MCF-7 to observe the secretion of exogenous Hsp90α. Antibodies against Hsp90α, Myc and His were used to detect the secreted Hsp90α. The result shows that the secreted Hsp90α was C-terminally truncated (FIG. 9A).

Using Myc-His-H as a template, the mutations of the final four amino acids (EEVD) of Hsp90α C-terminus was constructed. EE->AA represents the mutation of two EE to two Ala (using SEQ ID No. 11 and Hsp90α-EE-AA: GGC-CGCTCGAGTGTCTACTGCTGCCATGCGTGATGTG (SEQ ID No. 13) as primers), VD->AA means that VD were mutated to two Ala (using SEQ ID No. 11 and Hsp90α-VD-AA: GGCCGCTCGA GTTGCTGCTTCTTCCATGCGT-GATGTG (SEQ ID No. 14) as primers). All Ala represents the mutation of EEVD to four Ala (using SEQ ID No. 11 and Hsp90α-EEVD-AAAA: GGCCGCTCGAGTTGCTGCT-GCTGCCATGCG TGATGTG (SEQ ID No. 15) as primers), CM represents the deletion of last EEVD four amino acids (using SEQ ID No. 11 and Hsp90α-CΔ4-Xho: CCGCTC-GAGTCATGCGTGATGTGTCGTCATCTC (SEQ ID No. 16) as primers). Human breast cancer cell line MCF-7 was transiently transfected with these types of mutants to observe the secretion of exogenous Hsp90α (over-expressed Hsp90α, which is different from the endogenous one). The antibody against Hsp90α was used to detect the changes of secreted Hsp90α in the extracellular medium. The results show that four C-terminal amino acid residues regulate the secretion of Hsp90α. Any site-directed mutation or deletion of these four amino acid residues can lead to the secretion of Hsp90α without C-terminal truncation, which suggests that four C-terminal amino acid residues EEVD are deleted in the secreted extracellular Hsp90α (FIG. 9B).

Example 8

Examination of the Existing Form of Hsp90α in Human Plasma

We collected whole blood samples of liver cancer patients, which were centrifuged twice within 24 hours after collection, then detected Hsp90α in plasma using the method of immunoprecipitation and immunoblotting. First, specific rabbit polyclonal antibody against Hsp90α (Source: Labvision) was used for immunoprecipitation, and then a rabbit polyclonal antibody which can specifically recognize the Hsp90α C-terminal four amino acid residues EEVD (lab stock, antigen used for immunization used is a carrier protein coupled with three-repeated peptides of EEVD, synthesized from the SBS Genetech Co., Ltd.) was used to detect Hsp90α in plasma. As shown in FIG. 10, the EEVD antibody specifically recognize Hsp90α from whole cell lysate, but does not recognize Hsp90α in plasma, which indicates that intracellular Hsp90α is different from plasma Hsp90α, which lacks the four C-terminal amino acid residues EEVD. (FIG. 10).

Example 9

Detection of the Phosphorylated Form of Hsp90α in Plasma

Whole blood samples of the liver cancer patients were centrifuged twice to extract the plasma within 24 hours after collection. Then Hsp90α in plasma was detected using the method of immunoprecipitation and immunoblotting. First, specific rabbit polyclonal antibody against Hsp90α (Source: Labvision) was used to immunprecipitate plasma Hsp90α, then an antibody (Rabbit anti-phospho-(Ser/Thr) PKA substrate pAb, Cell signaling) which can specifically recognize the Thr90 phosphorylated Hsp90 was used to detect the Thr90 phosphorylation status of plasma Hsp90. As shown in FIG. 11, the Hsp90α in plasma is Thr90 phosphorylated.

Example 10

Detect the Concentration of Thr90 Phosphorylated Hsp90 in Plasma

Whole blood samples of both liver cancer patients and normal people were centrifuged twice to extract the plasma within 24 hours after collection. The relative level of Hsp90α in the plasma was detected using the method of sandwich ELISA. Protocol: firstly, using self-made rabbit polyclonal antibody S2 to coat the plate overnight at 4, then added 10-fold diluted plasma samples at 100 μl per well. After incubation at 37 for 2 hours, antibody which can specifically recognize the Thr90 phosphorylated Hsp90α (cell signal) was added. The plate is incubated at 37 for 2 hours; and then horseradish peroxidase conjugated goat anti-rabbit secondary antibodies were added and incubated for 1 hour. Finally o-phenylenediamine was added to detect the absorption at OD490 nm. The results show that the levels of Hsp90α in liver cancer patients are higher than those of normal people, P=0.003, Student t test, which indicates that the level of Thr90 phosphorylated Hsp90 is increased in liver cancer patients (FIG. 12).

Example 11

Detection of the Consistency of the Thr90 Phosphorylated Hsp90 Level in Plasma and the Total Hsp90α Content The levels of the Thr90 phosphorylated Hsp90 and the total amount of Hsp90α in liver cancer patients plasma (8 cases) were detected. The method to detect the total amount of plasma Hsp90α was the same as that used in example 5; the method to detect the level of Thr90 phosphorylated Hsp90 was the same as that used in example 10. The results show that the level of Thr90 phosphorylated plasma Hsp90 is consistent with the total amount of plasma Hsp90α, which further indicates that the phosphorylation of plasma Hsp90α is on Thr90, and the increment of the total amount of Hsp90α can represent the increment of Thr90 phosphorylated Hsp90α (FIG. 13).

Example 12

The Phosphorylation of Thr90 is Necessary for the Secretion of Hsp90α

Using pcDNA3.1-Myc-His-Hsp90α plasmid as the template (Also known as wild-type Hsp90α (WT Hsp90α)), mutant Hsp90α (T90A, threonine mutated to alanine) was constructed by quickchange PCR using the following primers: Hsp90α-T89A-Sense:GATCGAACTCTTGCAAT-TGTGGATACTGGAATTGGAATG(SEQIDNo17) and Hsp90α-T89-AntiSense: CATTCCAATTCCAGTATCCA-CAATTGCAAGAGT TCGATC (SEQ ID No. 18). T90A Hsp90α mutant can not be phosphorylated at Thr90. Human breast cancer cell line MCF-7 (purchased from ATCC, No. HTB-22) was transfected with wild-type Hsp90α (WT) or mutant Hsp90α (T90A). The medium was then collected and the secretion of exogenous Hsp90α was detected by anti-Hsp90α antibody.

The results show that overexpressed exogenous wild-type Hsp90α can be detected in the extracellular medium, while the T90A mutant can not be detected, which indicates that phosphorylation at residue Thr90 is a prerequisite for Hsp90α secretion. (FIG. 14).

Example 13

PP5 is Responsible for the Dephosphorylation of pT90-Hsp90α

The preparation of the Thr90 phosphorylated Hsp90α (pT90-Hsp90α): The recombinant human Hsp90α protein and recombinant protein kinase A (Promega Corporation USA) were incubated in a reaction buffer (NEB UK company) at 30° C. for 1 h, then pT90-Hsp90α protein was purified. After removing free phosphate by dialysis, the purified pT90-Hsp90α protein mixed with recombinant human PP5 protein were incubated at 30° C., the free phosphate released from the pT90-Hsp90α was detected using the non-radioactive serine/threonine phosphatase assay kit (Promega Corporation USA). Peptide substrate is a composition of the kit and was used as the positive control. As shown in FIG. 15A, when PP5 was incubated with the peptide substrate, the release of free phosphate was significantly increased, P value<0.005, Student t test, indicating that PP5 can directly dephosphorylate the peptide substrate (positive control). However, when PP5 was incubated with pT90-Hsp90α protein, the release of free phosphate was also significantly increased, P value<0.005, Student t test, indicating that PP5 can directly dephosphorylate pT90-Hsp90α.

The nucleotide sequence of PP5 (SEQ ID No. 6) was amplified from human liver cDNA library and constructed into the pcDNA3.1/Myc-His (−) (vector source: Invitrogen). The PP5 vector was transfected into and overexpressed in human breast cancer cell line MCF-7. On the other side, using the RNA interference technology, the expression of PP5 can also be knocked down using the siRNA with the sequence of 5'-ACTCGAACACCTCGCTAAAGAGCTC-3' (SEQ ID No. 7) (synthesized by Invitrogen). Then the status of Hsp90αThr90 phosphorylation was examined with the overexpression or knock down of PP5. As shown in FIG. 15B, with overexpression of human PP5, the Thr90 phosphorylated Hsp90α (pT90-Hsp90α) was significantly reduced (0.55 of the control). When the expression of human PP5 was suppressed, the Thr90 phosphorylated Hsp90α (pT90-Hsp90α) was significantly increased (1.58 of the control).

Example 14

Regulation of the Secretion of Hsp90α by Promoting or Inhibiting the Expression of PP5

PP5 can dephosphorylate Thr90 phosphorylated Hsp90α. Primers as follows were used to amplify PP5 from human liver cDNA library: PP5-NheI-For: CTAGCTAGCATGTAC-CCATACGACGTCCCAGACTACGCT (SEQ ID No. 19) and PP5-XhoI-Re: CCGCTCGAGTTAATGATGATGAT-GATG ATGCACGTGTACC (SEQ ID No. 20). The full length human PP5 was cloned into pcDNA3.1/Myc-His (−) (vector source: Invitrogen). Human breast cancer cell line MCF-7 was transfected with PP5 vector, then the secretion of Hsp90α from the cells was examined. The results showed that after overexpression of human PP5, the secretion of Hsp90α was significantly decreased (FIG. 16A).

On the other side, when the expression of human PP5 in MCF-7 cells was knocked down by RNA interference (against human PP5, Invitrogen), the secretion of Hsp90α was significantly increase (FIG. 16B).

Example 15

The Level of PP5 and the Tumor Malignancy

The relationship between the expression level of PP5 and the secretion of Hsp90α was examined in human breast cancer cell lines MCF-7, SKBR3, MDA-MB-453, 435s and 231 (ATCC, number, respectively HTB-22, -30, -131, -129, and HTB-26) using the method of Western blotting. MCF-7, SKBR3 breast cancer cell lines are less malignant cell lines. In the nude mice tumor model, these two cell lines can form primary tumors, but do not metastasize. MDA-MB-453, 435s and 231 are more malignant, They can not only form primary tumors, but also metastasize to distant organs in the nude mice tumor models. Thus MDA-MB-435s and 231 are often used to establish tumor metastasis models. In FIG. 17, secretion levels of Hsp90α by these five breast cancer cell lines correlate with their malignancy.

The results show that the cells, which express high level of PP5, secrete low level of Hsp90α; whereas cells with low expression of PP5 can secrete more Hsp90α (FIG. 17). Meanwhile, the results also show that the level of secreted Hsp90α is positively correlated, whereas the expression level of PP5 is negatively correlated with the tumor malignancy (FIG. 17). The level of secreted Hsp90α and its regulatory factors such as PP5 can be used to determine the tumor malignancy.

Example 16

The Expression Level of PP5 is Linked to Tumor Invasiveness

The wound healing model was employed to examine the relationship between the expression level of PP5 and tumor cell migration.

Human breast cancer cell line MCF-7 was transfected with human PP5 vector or PP5 siRNA. Then the cells were inoculated into 12-well plate. When the cells grew to confluence, pippete tips were used to scrape cells to form a "wound". The scraped cells were washed away, and the rest part of cells were cultured in fresh DMEM medium (GIBCO) at 37 in an incubator with 5% of $CO_2$. The images of the "wound" at the time of 0 h, 12 h, and 24 h were captured (FIG. 18A). The effect of PP5 expression on cell migration was examined by analyzing the "wound" healing rate. The results show that overexpression of PP5 inhibits MCF-7 cell migration, while PP5 siRNA can promote MCF-7 cell migration (FIG. 18B).

Example 17

The Effect of Plasma Hsp90α Specific Antibodies on Tumor Cell Migration

The wound healing model was used to detect the effect of plasma Hsp90α specific antibody on tumor cell migration.

MCF-7 or MDA-MB-231 cells (ATCC, No. HTB-22, respectively, and HTB-26) were inoculated into 12-well plate. When the cells grow to confluence, pippete tips were used to scrape cells to form a "wound". The scraped cells were washed away, and the rest part of cells were moved into fresh DMEM medium (GIBCO). Meanwhile, E9 (20 µg/ml), the specific mouse monoclonal antibody against Hsp90α, or control IgG (20 µg/ml) was added. Then the plate was incubated at 37, with 5% $CO_2$. Images of the "wound" after 0 h, 6 h, 12 h, 24 h, 48 h, and 72 h of incubation were captured (FIG. 18A). The effect of plasma Hsp90 specific antibodies on tumor cells migration was examined by monitoring the "wound" healing rate. As shown in FIG. 19, the specific antibody against plasma Hsp90α can significantly inhibit the migration of both MDA-MB-231 (FIG. 19A) and MCF-7 (FIG. 19B) (Inhibitory activity>40%).

Example 18

Detect the Effect of Plasma Hsp90α Specific Antibody on Tumor Metastasis

Nude mice with an average body weight of 20 g were purchased from Beijing Vital River Laboratory Animal Technology Co., Ltd. B16/F10 mouse melanoma cells (ATCC, number: CRL-6475) ($2 \times 10^5$) were injected into the mice via tail vein. Next day the mice were randomly divided into two groups (n=8): the control group (IgG was administered) and the Hsp90α Ab (mouse monoclonal antibody E9) treated group. The antibodies were administered once every other day with a dosage of 40 µg/mouse/time. Metastasis was detected 15 days after inoculation. As shown in FIG. 20, the specific antibody against plasma Hsp90α can completely inhibit the lymph node metastasis of B16/F10 cells (A), and 56% of the lung metastasis can be inhibited (B).

We claim:

1. An isolated polypeptide consisting of the amino acid sequence of SEQ ID No. 1.

2. The polypeptide according to claim 1, wherein one or more amino acid residues in the amino acid sequence of SEQ ID No. 1 selected from the group consisting of Thr90, Ser231, Ser263, Tyr309 and a combination thereof are phosphorylated.

3. The polypeptide according to claim 2, wherein Thr90 is phosphorylated.

* * * * *